United States Patent [19]

Machida et al.

[11] 4,415,567

[45] Nov. 15, 1983

[54] 7α-METHOXYCEPHALOSPORIN DERIVATIVES, AND ANTIBACTERIAL DRUGS CONTAINING THE SAME

[75] Inventors: Yoshimasa Machida, Wako; Isao Saito, Aza-Sori; Seiichiro Nomoto, Tokyo; Shigeto Negi, Kodaira; Hironori Ikuta, Tokyo; Kyosuke Kitoh, Kawagoe, all of Japan

[73] Assignee: Eisai Co., Ltd., Tokyo, Japan

[21] Appl. No.: 349,983

[22] Filed: Feb. 18, 1982

Related U.S. Application Data

[62] Division of Ser. No. 220,723, Dec. 29, 1980, Pat. No. 4,344,944.

[30] Foreign Application Priority Data

Mar. 4, 1980 [JP] Japan .................................. 55-26112
Jul. 8, 1980 [JP] Japan .................................. 55-92199

[51] Int. Cl.$^3$ ................. C07D 501/57; A61K 31/545
[52] U.S. Cl. ........................................ 424/246; 544/21
[58] Field of Search ....................... 544/28, 25, 26, 24, 544/21, 27, 22; 424/246

[56] References Cited

U.S. PATENT DOCUMENTS 4,285,941  8/1981  Machida et al. ..................... 544/27

Primary Examiner—Nicholas S. Rizzo
Attorney, Agent, or Firm—Wenderoth, Lind & Ponack

[57] ABSTRACT

Novel 7α-methoxycephalosporin derivatives, their pharmaceutically acceptable salts, process for the preparation thereof, and antibacterial drugs involving the derivative or salt. The derivatives or salts are effective against the Gram-positive bacteria and the Gram-negative bacteria.

5 Claims, No Drawings

7α-METHOXYCEPHALOSPORIN DERIVATIVES, AND ANTIBACTERIAL DRUGS CONTAINING THE SAME

This application is a division of application Ser. No. 220,723, filed Dec. 29, 1980 (now U.S. Pat. No. 4,344,944).

This invention relates to novel 7α-methoxycephalosporin derivatives represented by the formula (I):

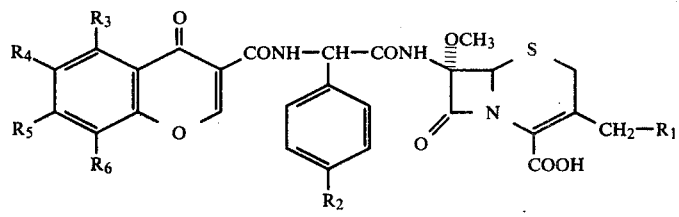

wherein $R_1$ represents lower alkanoyloxy, carboxyalkylthio or nitrogen-containing heterocyclic-thio which may have substituent; $R_2$ represents hydrogen or hydroxy; $R_3$, $R_4$, $R_5$, and $R_6$ each represents a group selected from the class consisting of hydrogen, hydroxy, lower alkanoyloxy, alkoxy, alkyl, halogen, aralkyloxy, nitro, alkoxycarbonyloxy, and chloro-substituted alkoxycarbonyloxy, pharmaceutically acceptable salts thereof, the process for the preparation thereof, and antibacterial drugs comprising them.

Among the substituents $R_3$, $R_4$, $R_5$ and $R_6$ in the formula (I), one can mention lower alkanoyloxy groups such as acetoxy, propionyloxy and the like; alkoxy groups such as methoxy, ethoxy, propoxy and the like; alkyl groups such as methyl, ethyl, n-propyl, i-propyl, n-butyl, t-butyl and the like; halogen atoms such as chlorine, bromine and the like; aralkyloxy groups such as benzyloxy, phenethyloxy and the like; alkoxycarbonyloxy groups such as methoxycarbonyloxy, ethoxycarbonyloxy and the like; and chloro-substituted alkoxycarbonyloxy groups such as 2,2,2-trichloroethoxycarbonyloxy.

Among the substituent $R_1$, one can mention carboxyalkylthio groups such as carboxymethylthio, carboxyethylthio and the like, as well as lower alkanoyloxy group such as acetoxy, propionyloxy and the like.

With reference to the wording "nitrogen-containing heterocyclic-thio which may have substituent" which is represented by $R_1$ in the formula (I), it means a substituted or unsubstituted heterocyclic-thio group containing one or more nitrogen atoms as hetero atoms. The said nitrogen-containing heterocyclic group may be a mono- or polycyclic group. These nitrogen-containing heterocyclic groups may contain one or more nitrogen atoms only as hetero atoms or atoms, or they may also contain other hetero atom or atoms such as sulfur and oxygen in addition to nitrogen. Representative of such nitrogen-containing heterocyclic groups are, for example, pyrrolyl, pyridyl and its N-oxide, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadizolyl, morpholino, benzothiazolyl, benzoxazolyl, and the like. These groups may have one or more substituents. The examples of such substituents are alkyl groups such as methyl, ethyl, propyl, isopropyl and the like; dialkyl-aminoalkyl groups such as dimethylaminoethyl, dimethylaminoethyl, diethylaminoethyl, and the like, alkoxycarbonylalkyl groups such as methoxycarbonylmethyl, ethoxycarbonylmethyl, and the like, and carboxyalkyl groups such as carboxymethyl, carboxyethyl, and the like.

As the pharmaceutically acceptable salts of the compound of the formula (I), one can mention alkali metal salt such as salts of sodium, potassium and the like, as well as salts of calcium, ammonium, triethylamine dicyclohexylamine, procaine and the like. Representative of these salts are usually carboxylate, although, when $R_5$ in the formula (I) is hydroxy, one can also mention the salts of this hydroxy moiety.

The compound of this invention can be prepared by the following procedure:

A compound represented by the formula (II):

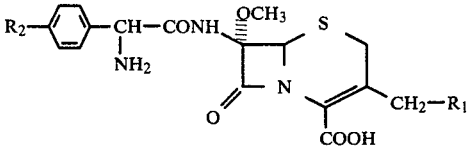

wherein $R_1$ and $R_2$ are the same as previously defined, or a salt or hydrate thereof is reacted with a compound represented by the formula (III):

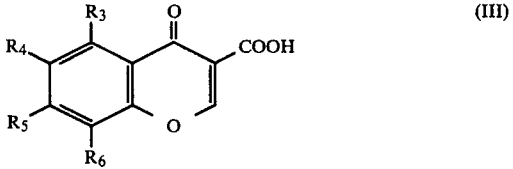

wherein $R_3$, $R_4$, $R_5$ and $R_6$ are the same as previously defined, or a reactive derivative thereof, to produce the compound of the formula (I) of this invention, and if required to form the salt thereof.

In this reaction, when the compound of the formula (III) used is a carboxylic acid (—COOH), the reaction is preferably effected in the presence of a condensation agent, for example, N,N'-dicyclohexylcarbodiimide, N,N'-diethylcarbodiimide, N-cyclohexyl-N'-morpholinoethylcarbodiimide, phosphorous acid ethyl ester, phosphorus oxy chloride, oxalyl chloride, and the like. When a reactive derivative from the carboxyl group of the compound of the formula (III) is used, the reactive derivative includes acid halides such as acid chloride, acid bromide and the like; symmetric acid anhydrides; mixed anhydrides derived from chlorocarbonic ester, trimethylacetic acid, diphenylacetic acid and the like; active esters derived from 2-mercaptopyridine, cyanomethanol, p-nitrophenol, 2,4-dinitrophenol, pentachlorophenol and the like; and active acid amides derived from N-acylsacharin, N-acylphthalimide and the like.

The reaction can be carried out in an inert solvent at the temperature from −50° C. to 50° C. preferably from −20° C. to 30° C. in the presence or absence of a basic reagent or silylating agent.

Representative of the inert solvent may be acetone, tetrahydrofuran, dimethylacetamide, dimethylformamide, dioxane, dichloromethane, chloroform, benzene, toluence, ethyl acetate or the mixture thereof.

Representative of the basic reagent may be, for example, alkali hydroxides such as sodium hydroxide, potassium hydroxide and the like; alkali hydrogen carbonates such as sodium hydrogen carbonate, potassium hydrogen carbonate and the like; amines such as triethylamine, pyridine, dimethylaniline, N-methylmorpholine and the like.

Representative of the silylating agent may be, for example, N,O-bis(trimethylsilyl)acetamide, hexamethyldisilazane, trimethylsilylacetamide and the like.

The compound of the formula (III), which is a starting material in the synthetic process according to this invention, can be produced by oxidation of the corresponding chromone aldehyde using an oxidizing agent such as sodium chloritesulfamic acid, Jones reagent (refer to "Reagents for Organic Synthesis" vol. 1 Page 142) and the like. When hydroxyl group is included in the substituents of the compound of the formula (III), the compound can be produced by oxidizing the chromone aldehyde which contains acyloxy group on the position of the hydroxyl group, according to the procedure described above, followed by hydrolysis of the oxidation product. The acid halide of the compound of the formula (III) can be produced by reacting the compound of the formula (III) with a halogenating agent such as phosphorus pentachloride, thionyl chloride and the like.

The chromone aldehyde can be prepared by a conventional method, for example, the method described in "Tetrahedron" Vol. 30, P.3553 (1974), or the like.

The compound of the Formula II which is another starting material for the synthetic method of this invention can be prepared by the methods, for example, described in Japanese Patent Application Laid-open No. 931/72, Japanese Patent Application Laid-open No. 68193/77, etc.

Among the compounds of this invention, the compound of the formula (I) wherein $R_1$ is carboxyalkylthio, nitrogen-containing heterocyclic-thio which may have substituent, can be also prepared as follows;

A compound represented by the formula (IV)

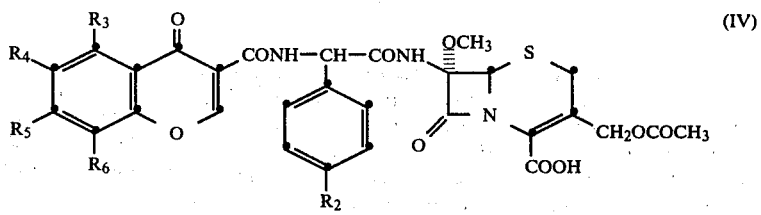

wherein $R_2$, $R_3$, $R_4$, $R_5$ and $R_6$ are the same as heretofore defined, or a salt or hydrate thereof is reacted with the compound of the formula (V):

$$R_7-H$$

wherein $R_7$ represents carboxyalkylthio or nitrogen-containing heterocyclic-thio which may have substituent.

This reaction can be carried out in a solvent such as water, a buffer solution, at the temperature of 50° C.-70° C. in the presence of sodium hydrogen carbonate, sodium hydroxide and/or the like.

Further, among the compounds of this invention, the compound of the formula (I) wherein $R_1$ is 5-tetrazolylthio, 2-(1,3,4-thiadiazolyl)thio, or 2-(1,3,4-oxadiazolyl)thio, each having carboxymethyl, can be also prepared as follows:

A compound represented by the formula (VI)

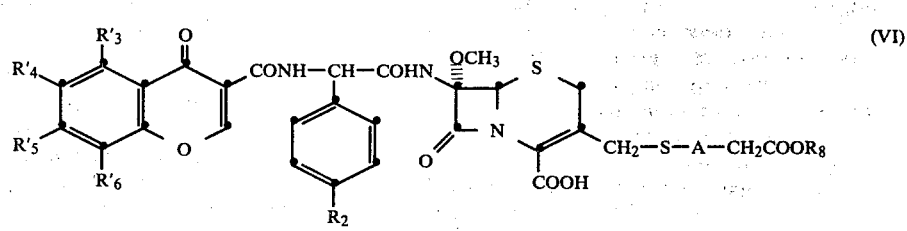

wherein $R_2$ is the same as set forth above, $R'_3$, $R'_4$, $R'_5$, and $R'_6$ are hydrogen or hydroxyl, A represents tetrazole ring, 1,3,4-thiadiazole ring, or 1,3,4-oxidazole ring, and $R_8$ represents lower alkyl, or a salt thereof is hydrolyzed in the presence of a base, to obtain the compound represented by the formula (VII):

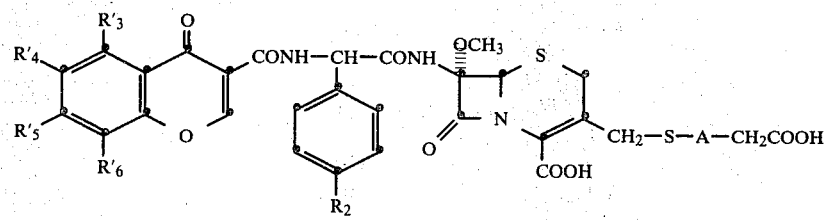

(VII)

wherein $R_2$, $R'_3$, $R'_4$, $R'_5$, $R'_6$ and A are the same as set forth above.

There may be mentioned as a base sodium hydroxide, potassium hydroxide, sodium carbonete, sodium hydrogen carbonate, and the like.

Among the compounds of this invention, the compounds which contain hydroxyl groups as the substituent $R_3$, $R_4$, $R_5$ or $R_6$ on the chromone moiety may be prepared according to the method described above from a starting material which contains hydroxyl groups, or may be prepared by hydrolyzing the compound of this invention which contains, on the position of the hydroxyl groups, lower alkanoyloxy, alkoxycarbonyloxy or chloro-substituted alkoxycarbonyloxy.

Representative compounds of this invention are the following compounds and their sodium salts:

7β-[D-2-(Chromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(6,7-Diacetoxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(6,7-Diacetoxychromone-3-carboxamido)-2-(4-hydroxyphenyl)acetamido]-7α-methoxy-3-[(5-methyl-2-1,3,4-thiadiazolyl)]thiomethyl-3-cephem-4-carboxylic acid 7β-[D-2-(6,7-Dihydroxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(6,7-Dihydroxychromone-3-carboxamido)-2-phenylacetamido]-7α-methoxy-3-(1-methyl-5-tetrazolyl)thiomethyl-3-cephem-4-carboxylic acid 7β-[D-2-(6,7-Dihydroxychromone-3-carboxamido)-2-(4-hydroxyphenyl)acetamido]-7α-methoxy-3-[5-methyl-2-(1,3,4-thiadiazolyl)]thiomethyl-3-cephem-4-carboxylic acid 7β-[D-2-(6,7-Dihydroxychromone-3-carboxamido)-2-phenylacetamido]-7α-methoxy-3-[-(5-methyl-2-(1,3,4-thiadiazolyl)]thiomethyl-3-cephem-4-carboxylic acid 7β-[D-2-(6,7-Dihydroxychromone-3-carboxamido)-2-(4-hydroxyphenyl)acetamido]-7α-methoxy-3-acetoxymethyl-3-cephem-4-carboxylic acid 7β-[D-2-(6,7-Dihydroxychromone-3-carboxamido)-2-phenylacetamido]-7α-methoxy-3-acetoxymethyl-3-cephem-4-carboxylic acid 7β-[D-2-(6,7-Diacetoxychromone-3-carboxamido)-2-(4-hydroxyphenyl)acetamido]-7α-methoxy-3-acetoxymethyl-3-cephem-4-carboxylic acid 7β-[D-2-(7,8-Diacetoxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(7,8-Diacetoxychromone-3-carboxamido)-2-(4-hydroxyphenyl)acetamido]-7α-methoxy-3-[2-(5-methyl-2-(1,3,4-thiadiazolyl)thiomethyl]-3-cephem-4-carboxylic acid 7β-[D-2-(7,8-Dihydroxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(7,8-Dihydroxychromone-3-carboxamido)-2-(4-hydroxyphenyl)acetamido]-7α-methoxy-3-[(5-methyl-2-(1,3,4-thiadiazolyl)]thiomethyl-3-cephem-4-carboxylic acid 7β-[D-2-(7,8-Dihydroxychromone-3-carboxamido)-2-phenylacetamido]-7α-methoxy-3-acetoxymethyl-3-cephem-4-carboxylic acid 7β-[D-2-(6,7,8-Trihydroxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(6,7,8-Trihydroxychromone-3-carboxamido)-2-(4-hydroxyphenyl)acetamido]-7α-methoxy-3-[(5-methyl-2-(1,3,4-thiadiazolyl)]thiomethyl-3-cephem-4-carboxylic acid 7β-[D-2-(6,7,8-Triacetoxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(6,7,8-Triacetoxychromone-3-carboxamido)-2-(4-hydroxyphenyl)acetamido]-7α-methoxy-3-[5-methyl-2-(1,3,4-thiadiazolyl)]thiomethyl-3-cephem-4-carboxylic acid 7β-[D-2-(5-Methoxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-(6-Nitrochromone-3-carboxamido)-2-phenylacetamido]-7α-methoxy-3-acetoxymethyl-3-cephem-4-carboxylic acid 7β-[D-2-(7-Chlorochromone-3-carboxamido)-2-phenylacetamido]-7α-methoxy-3-acetoxymethyl-3-cephem-4-carboxylic acid 7β-[D-2-(7-Benzyloxy-8-methylchromone-3-carboxamido)-2-phenylacetamido]-7α-methoxy-3-acetoxymethyl-3-cephem-4-carboxylic acid 7β-[D-2-(6,7-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid;

7β-[D-2-(6,7-Dihydroxychromone-3-carboxamido)-2-(4-hydroxyphenyl)acetamido]-7α-methoxy-3-(1-methoxycarbonylmethyl-5-tetrazolyl)thiomethyl-3-cephem-4-carboxylic acid;

7β-[D-2-(7,8-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid;

7β-[D-2-(7,8-Dihydroxychromone-3-carboxamido)-2-(4-hydroxyphenyl)acetamido]-7α-methoxy-3-(1-methoxycarbonylmethyl-5-tetrazolyl)thiomethyl-3-cephem-4-carboxylic acid;

7β-[D-2-(6,8-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid 7β-[D-2-[6,7-Bis(ethoxycarbonyloxy)chromone-3-carboxamido]-2-(4-hydroxyphenyl)acetamido]-7α-methoxy-3-(1-carboxymethyl-5-tetrazolyl)thiomethyl-3-cephem-4-carboxylic acid 7β-[D-2-[6,7-Bis(ethoxycarbonyloxy)chromone-3-carboxamido]-2-phenylacetamido]-7α-methoxy-3-(1-carboxymethyl-5-tetrazolyl)-thiomethyl-3-cephem-4-carboxylic acid 7β-[D-2-[6,7-Bis(ethoxycarbonyloxy)chromone-3-carboxamido]-2-(4-hydroxyphenyl)acetamido]-7α-methoxy-3-acetoxymethyl-3-cephem-4-carboxylic acid 7β-[D-2-[6,7-Bis(ethoxycarbonyloxy)chromone-3-carboxamido]-2-phenylacetamido]-7α-methoxy-3-acetoxymethyl-3-cephem-4-carboxylic acid 7β-[D-2-[6,7-Bis(ethoxycarbonyloxy)chromone-3-carboxamido]-2-(4-hydroxyphenyl)acetamido]-7α-methoxy-3-(1-methyl-5-tetrazolyl)thiomethyl-3-cephem-4-carboxylic acid 7β-[D-2-[6,7-Bis(ethoxycarbonyloxy)chromone-3-carboxamido]-2-(4-hydroxyphenyl)acetamido]-7α-methoxy-3-[5-methyl-2-(1,3,4-thiadiazolyl)]thiomethyl-3-cephem-4-carboxylic acid 7β-[D-2-[6,7-Bis(ethoxycarbonyloxy)chromone-3-carboxamido]-2-(4-hydroxyphenyl)acetamido]-7α-methoxy-3-[5-carboxymethyl-2-(1,3,4-thiadiazolyl)]thiomethyl-3-cephem-4-carboxylic acid 7β-[D-2-[6,7-Bis(ethoxycarbonyloxy)chromone-3-carboxamido]-2-(4-hydroxyphenyl)acetamido]-7α-methoxy-3-[5-carboxymethyl-2-(1,3,4-oxadiazolyl)]-thiomethyl-3-cephem-4-carboxylic acid 7β-[D-2-[6,7-Bis(ethoxycarbonyloxy)chromone-3-arboxamido]-2-(4-hydroxyphenyl)acetamido]-7α-methoxy-3-(1-methoxycarbonylmethyl-5-tetrazolyl)-thiomethyl-3-cephem-4-carboxylic acid 7β-[D-2-[6,7-Bis(2,2,2-trichloroethoxycarbonyloxy)-chromone-3-carboxamido]-2-(4-hydroxyphenyl)acetamido]-7α-methoxy-3-(1-carboxymethyl-5-tetrazolyl)thiomethyl-3-cephem-4-carboxylic acid 7β-[D-2-[6,7-Bis(2,2,2-trichloroethoxycarbonyloxy)-chromone-3-carboxamido]-2-phenylacetamido]-7α-methoxy-3-(1-carboxymethyl-5-tetrazolyl)thiomethyl-3-cephem-4-carboxylic acid 7β-[D-2-[6,7-Bis(2,2,2-trichloroethoxycarbonyloxy)-chromone-3-carboxamido]-2-phenylacetamido]-7α-methoxy-3-acetoxymethyl-3-cephem-4-carboxylic acid 7β-[D-2-[6,7-Bis(2,2,2-trichloroethoxycarbonyloxy)-chromone-3-carboxamido]-2-(4-hydroxyphenyl)acetamido]-7α-methoxy-3-acetoxymethyl-3-cephem-4-carboxylic acid 7β-[D-2-[6,7-Bis(2,2,2-trichloroethoxycarbonyloxy)-chromone-3-carboxamido]-2-(4-hydroxyphenyl)acetamido]-7α-methoxy-3-(1-methyl-5-tetrazolyl)-thiomethyl-3-cephem-4-carboxylic acid 7β-[D-2-[6,7-Bis(2,2,2-trichloroethoxycarbonyloxy)-chromone-3-carboxamido]-2-(4-hydroxyphenyl)acetamido]-7α-methoxy-3-(1-methoxycarbonylmethyl-5-tetrazolyl)thiomethyl-3-cephem-4-carboxylic acid 7β-[D-2-(6,7-Dihydroxychromone-3-carboxamido)-2-(4-hydroxyphenyl)acetamido]-7α-methoxy-3-[5-carboxymethyl-2-(1,3,4-thiadiazolyl)]thiomethyl-3-cephem-4-carboxylic acid 7β-[D-2-(6,7-Dihydroxychromone-3-carboxamido)-2-phenylacetamido]-7α-methoxy-3-[5-carboxymethyl-2-(1,3,4-thiadiazolyl)]thiomethyl-3-cephem-4-carboxylic acid 7β-[D-2-(7,8-Dihydroxychromone-3-carboxamido)-2-(4-hydroxyphenyl)acetamido]-7α-methoxy-3-[5-carboxymethyl-2-(1,3,4-thiadiazolyl)]thiomethyl-3-cephem-4-carboxylic acid 7β-[D-2-(7,8-Dihydroxychromone-3-carboxamido)-2-phenylacetamido]-7α-methoxy-3-[5-carboxymethyl-2-(1,3,4-thiadiazolyl)]thiomethyl-3-cephem-4-carboxylic acid 7β-[D-2-(6,7-Dihydroxychromone-3-carboxamido)-2-(4-hydroxyphenyl)acetamido]-7α-methoxy-3-[5-carboxymethyl-2-(1,3,4-oxadiazolyl)]thiomethyl-3-cephem-4-carboxylic acid 7β-[D-2-(6,7-Dihydroxychromone-3-carboxamido)-2-phenylacetamido]-7α-methoxy-3-[5-carboxymethyl-2-(1,3,4 oxadiazolyl)]thiomethyl-3-cephem-4-carboxylic acid 7β-[D-2-(7,8-Dihydroxychromone-3-carboxyamido)-2-(4-hydroxyphenyl)acetamido]-7α-methoxy-3-[5-carboxymethyl-2-(1,3,4-oxadiazolyl)]thiomethyl-3-cephem-4-carboxylic acid 7β-[D-2-(7,8-Dihydroxychromone-3-carboxamido)-2-phenylacetamido]-7α-methoxy-3-[5-carboxymethyl-2-(1,3,4-oxadiazolyl)]thiomethyl-3-cephem-4-carboxylic acid 7β-[D-2-(6,7-Dihydroxychromone-3-carboxamido)-2-(4-hydroxyphenyl)acetamido]-7α-methoxy-3-carboxymethylthiomethyl-3-cephem-4-carboxylic acid 7β-[D-2-(6,7-Dihydroxychromone-3-carboxamido)-2-phenylacetamido]-7α-methoxy-3-carboxymethylthiomethyl-3-cephem-4-carboxylic acid 7β-[D-2-(6,7-Dihydroxychromone-3-carboxamido)-2-(4-hydroxyphenyl)acetamido]-7α-methoxy-3-[1-[2-(N,N-dimethylamino)ethyl]-5-tetrazolyl]thiomethyl-3-cephem-4-carboxylic acid 7β-[D-2-(6,7-Dihydroxychromone-3-carboxamido)-2-phenylacetamido]-7α-methoxy-3-[1-[2-(N,N-dimethylamino)ethyl]-5-tetrazolyl]thiomethyl-3-cephem-4-carboxylic acid 7β-[D-2-(6,7-Dihydroxychromone-3-carboxamido)-2-(4-hydroxyphenyl)acetamido]-7α-methoxy-3-(1-ethyl-5-tetrazolyl)thiomethyl-3-cephem-4-carboxylic acid 7β-[D-2-(6,7-Dihydroxychromone-3-carboxamido)-2-(4-hydroxyphenyl)acetamido]-7α-methoxy-3-[2-(1,3,4-thiadiazolyl)]thiomethyl-3-cephem-4-carboxylic acid 7β-[D-2-(6,7-Dihydroxychromone-3-carboxamido)-2-(4-hydroxyphenyl)acetamido]-7α-methoxy-3-[5-methyl-2-(1,3,4-oxadiazolyl)]thiomethyl-3-cephem-4-carboxylic acid 7β-[D-2-(6,7-Dihydroxychromone-3-carboxamido)-2-phenylacetamido]-7α-methoxy-3-(1-carboxymethyl-5-tetrazolyl)thiomethyl-3-cephem-4-carboxylic acid 7β-[D-2-(6,7-Diacetoxychromone-3-carboxamido]-2-(4-hydroxyphenyl)acetamido]-7α-methoxy-3-(1-carboxymethyl-5-tetrazolyl)thiomethyl-3-cephem-4-carboxylic acid 7β-[D-2-(6,7-Diacetoxychromone-3-carboxamido]-2-(4-hydroxyphenyl)acetamido]-7α-methoxy-3-[5-carboxymethyl-2-(1,3,4-thiadiazolyl)]thiomethyl-3-cephem-4-carboxylic acid 7β-[D-2-(6,7-Diacetoxychromone-3-carboxamido]-2-(4-hydroxyphenyl)acetamido]-7α-methoxy-3-[5-car boxymethyl-2-(1,3,4-oxadiazolyl)]thiomethyl-3-cephem-4-carboxylic acid.

The compounds of this invention exhibit excellent antibacterial activity, and are effective against the Gram-positive bacteria and the Gram-negative bacteria. Particularly, the compounds of this invention are effective against those bacteria such as *Pseudomanas aeruginosa, Serratia marcescens,* and the like that cause hardly curable infections, as well as the bacteria producing β-lactamase.

The acute toxicity values [$LD_{50}$(mouse, oral)] for the following compounds of this invention were over 5 g/kg:

7β-[D-2-(6,7-Dihydroxychromone-3-carboxamido)-2-(4-hydroxyphenyl)acetamido]-7α-methoxy-3-(1-methyl-5-tetrazolyl)thiomethyl]-3-cephem-4-carboxylic acid;

7β-[D-2-(6,7-Dihydroxychromone-3-carboxamido)-2-(4-hydroxyphenyl)acetamido]-7α-methoxy-3-[5-methyl-2-(1,3,4-thiadiazolyl)]thiomethyl-3-cephem-4-carboxylic acid;

Disodium salt of 7β-[D-2-(6,7-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid;

7β-[D-2-[6,7-Bis(ethoxycarbonyloxy)chromone-3-carboxamido]-2-(4-hydroxyphenyl)acetamido]-7α-methoxy-3-(1-methoxycarbonylmethyl-5-tetrazolyl)-thiomethyl-3-cephem-4-carboxylic acid;

7β-[D-2-[6,7-Bis(2,2,2-trichroloethoxy-carbonyloxy)-chromone-3-carboxamido]-2-(4-hydroxyphenyl)acetamido]-7α-methoxy-3-(1-methyl-5-tetrazolyl)-thiomethyl-3-cephem-4-carboxylic acid;

7β-[D-2-(6,7-Dihydroxychromone)-3-carboxamido]-2-(4-hydroxyphenyl)acetamido]-3-[5-carboxymethyl-2-(1,3,4-thiadiazolyl)]thiomethyl-3-cephem-4-carboxylic acid.

The dose of the compound of this invention, when used as antibacterial drugs, may range generally from 2 to 300 mg/kg/day, preferably from 10 to 100 mg/kg/day. This medicine can be administered orally in the form of powder, granule, tablet, capsule, syrup, and the like, or parenterally in the form of injection, suppository, and the like.

These preparations can be provided by conventional processes. The preparations of powder, granule, tablet and capsule can be provided using appropriately excipients such as lactose, starch, white sugar, glucose, crystallized cellulose, and the like; disintegrants, such as, starch, calcium salt of carboxymethylcellulose, calcium carbonate, dextrine, and the like; binders such as polyvinyl alcohol, ethylcellulose, gum arabic, tragacanth, hydroxypropylcellulose; and lubricants such as calcium stearate, magnesium stearate, talc, and the like.

The preparations of syrup can be provided using appropriately sweetenings such as white sugar, sorbitol, glucose, fructose, and the like; dispersants and thickenners such as gum arabic, tragacanth, sodium salt of carboxymethylcellulose, methylcellulose, sodium arginate, and the like.

The preparations for injection can be provided using isotonic agents such as glucose, sodium chloride, sorbitol, and the like, and if required, suspending agents, surfactants, pH controlling agents, or the like. Alternatively, the preparation for injection may be in the form of powder which can be dissolved prior to administration.

The suppository can be provided using a basis such as cacao butter, polyethylene glycol, Witepsol (trade mark, Dynamite-Nobel-AG), and the like and, if required, a surfactant.

The following experiments and examples illustrate this invention, but are not to be construed as limiting the scope thereof.

EXPERIMENT I

Preparation of chromone-3-carboxylic acids which are the intermediates of the compounds of this invention.

(A) 6,7-Diacetoxychromone-3-carboxylic acid 6,7-Diacetoxychromone-3-carboxaldehyde (17.8 g) was dissolved in acetone (1 liter). To this solution was added dropwise with stirring Jones reagent (32.8 ml) which had been previously prepared by dissolving chromic acid (133.6 g) in concentrated sulfuric acid (115 ml) diluted with water to a volume of 500 ml.

The reaction mixture was concentrated to 100 ml, and poured into water (900 ml). The precipitates (6.5 g) were collected by filtration, and recrystallized from ethyl acetate to obtain the desired compound (5.9 g).

(B) 6,7-Dihydroxychromone-3-carboxylic acid

To 6.7-diacetoxychromone-3-carboxylic acid (15.3 g) produced in (A) were added acetic acid (300 ml) and concentrated hydrochloric acid (100 ml), and the mixture was stirred for 20 minutes at about 70° C., then cooled. The precipitates were collected by filtration, and recrystallized from dimethylformamide-water to obtain the desired compound (8.9 g).

(C) 6,7-Bis(ethoxycarbonyloxy)chromone-3-carboxylic acid (1) 4,5-Bis(ethoxycarbonyloxy)-2-hydroxyacetophenone 2,4,5-Trihydroxyacetophenone (3.36 g) was dissolved in ethyl acetate (150 ml), and pyridine (3.24 ml) was added at about −5° C. with stirring. Then, a solution (50 ml) of ethyl chloroformate (3.8 ml) in ethyl acetate was added dropwise over 30 minutes. The mixture was stirred for 10 minutes at the same temperature. The resulting precipitate was collected by filtration and washed three times with ethyl acetate (10 ml). The washings and the filtrate were combined, and the mixture was washed with water (once) and a saturated aqueous solution of sodium chloride (three times) and dried over magnesium sulfate. The solvent was distilled off, and the residue was recrystallized from ethyl ether-ethanol. The crystals were collected by filtration, and washed with ethanol and n-hexane and dried to afford the desired product (4.60 g).

Melting Point: 58°–60° C.

(2) 6,7-Bis(ethoxycarbonyloxy)chromone-3-carboxaldehyde

The above compound (1) (37.47 g) was dissolved in dimethyl formamide (300 ml). The solution was cooled to about −5° C., and with stirring, phosphorus oxychloride (120 ml) was added dropwise over 40 minutes. The mixture was stirred at room temperature for 5.5 hours. The reaction mixture was added to ice water (3 liters) and stirred for 20 minutes. The resulting precipitate was collected by filtration, washed with water, and dissolved in ethyl acetate. The ethyl acetate solution was washed with water three times and dried over magnesium sulfate. The solvent was distilled off, and ethanol was added to the residue to solidify it. The solidified product was collected by filtration, washed with ethanol and n-hexane, and then dried to afford the desired product (28.5 g).

Melting Point: 101°–102° C.

Other compounds were prepared by the processes according to (A)–(C). The properties of the resulting compounds were shown in the following Table.

TABLE I-1

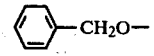

| No. | R$_3$ | R$_4$ | (III) R$_5$ | R$_6$ | Infrared Absorption Spectrum (cm$^{-1}$ nujol) | Molecular Formula Melting Point (°C.) | Elemental Analysis (%) Calculated Found | |
|---|---|---|---|---|---|---|---|---|
| | | | | | | | C | H |
| 1 | H | H | H | H | 1755, 1620–1650 | C$_{10}$H$_6$O$_4$ <br> 200–201 | 63.16 <br> 63.22 | 3.18 <br> 2.96 |
| 2 | H | CH$_3$COO— | CH$_3$COO— | H | 1780, 1760, 1730, 1620 | C$_{14}$H$_{10}$O$_8$ <br> 186–188 | 54.91 <br> 54.95 | 3.29 <br> 3.08 |
| 3 | H | HO— | HO— | H | 3370, 3300, 1730, 1635, 1620 | C$_{10}$H$_6$O$_6$ <br> >300 | 54.06 <br> 54.05 | 2.72 <br> 2.60 |
| 4 | H | H | CH$_3$COO— | CH$_3$COO— | 1780, 1760, 1740, 1625 | C$_{14}$H$_{10}$O$_5$ <br> 178–179 | 54.91 <br> 54.90 | 3.29 <br> 3.25 |
| 5 | H | H | HO— | HO— | 3380, 3275, 1725, 1620 | C$_{10}$H$_6$O$_6$ <br> 265–270* | 54.06 <br> 53.65 | 2.72 <br> 2.53 |
| 6 | CH$_3$O— | H | H | H | 1745, 1630 | C$_{11}$H$_8$O$_5$ <br> 217–218 | 60.00 <br> 60.03 | 3.66 <br> 3.66 |
| 7 | H | NO$_2$— | H | H | 2800, 1740, 1620 1590, 1570, 1525 | C$_{10}$H$_5$NO$_6$ <br> 208–212 | 51.07 <br> 51.08 | 2.15 <br> 1.98 |
| 8 | H | H | Cl | H | 1755, 1610 | C$_{10}$H$_5$ClO$_4$ <br> 214–215 | 53.48 <br> 53.40 | 2.24 <br> 2.14 |
| 9 | H | H | ⟨phenyl⟩—CH$_2$O— | CH$_3$— | 1730, 620 | C$_{18}$H$_{14}$O$_5$ <br> 223–226 | 69.67 <br> 69.48 | 4.55 <br> 4.44 |
| 10 | H | CH$_3$COO— | CH$_3$COO— | CH$_3$COO— | 1780, 1690, 1650, 1615 | C$_{16}$H$_{12}$O$_{10}$ <br> 192–195 | 52.76 <br> 52.65 | 3.32 <br> 3.30 |
| 11 | H | HO— | HO— | HO— | 1720, 1630 | C$_{10}$H$_6$O$_7$ <br> >280 | 50.43 <br> 50.22 | 2.54 <br> 2.61 |
| 12 | H | C$_2$H$_5$OCOO— | C$_2$H$_5$OCOO— | H | 1765, 1625 | C$_{16}$H$_{14}$O$_{10}$ <br> 107–109° C. | 52.47 <br> 52.57 | 3.85 <br> 3.63 |
| 13 | H | Cl$_3$CCH$_2$OCOO— | Cl$_3$CCH$_2$OCOO— | H | 1780, 1620, 1590, 1570 | C$_{16}$H$_8$Cl$_6$O$_{10}$ <br> 166–167° C. | 33.54 <br> 33.46 | 1.41 <br> 1.35 |

*with decomposition (3) 6,7-Bis(ethoxycarbonyloxy)chromone-3-carboxylic acid

The compound (1.05 g) obtained in (2) was dissolved in of dichloromethane (31.5 ml) and a solution of 1.05 g of sulfamic acid in water (18.9 ml) was added at 10° C. with stirring. Then, a solution of sodium chlorite (525.6 mg) in water (1.2 ml) was added. The solution was stirred at the same temperature for 1 hour, and allowed to separate. The dichloromethane layer was washed with water (once) and then with a saturated aqueous solution of sodium chloride (twice), and dried over magnesium sulfate. The solvent was distilled off, and ethyl ether was added to the residue to triturate it. The triturated product was collected by filtration, and dried to afford the desired product (950 mg).

EXAMPLE 1

7β-[D-2-(6,7-Diacetoxychromone-3-carboxamido)-2-(4-hydroxyphenyl)acetamido]-7α-methoxy-3-(1-methyl-5-tetrazolyl)thiomethyl-3-cephem-4-carboxylic acid (a) 6,7-Diacetoxychromone-3-carbonyl chloride A mixture of 6,7-diacetoxychromone-3-carboxylic acid (18.4 g), benzene (450 ml), 8.6 g of thionyl chloride (8.6 g) and dimethylformamide (3 ml) was refluxed for one hour and then cooled to room temperature. To the reaction mixture was added hexane (300 ml) and the precipitate separated out was recovered by filtration. There was thus obtained the desired product (17.6 g).

Infrared absorption spectrums, (cm$^{-1}$, Nujol): 1780, 1755, 1660, 1625

(b) 7β-[D-2-(6,7-Diacetoxychromone-3-carboxamido)-2-(4-hydroxyphenyl)acetamido]-7α-methoxy-3-(1-methyl-5-tetrazolyl)thiomethyl]-3-cephem-4-carboxylic acid 7β-[D-2-Amino-(4-hydroxyphenyl)acetamido]-7α-methoxy-3-(1-methyl-5-tetrazolyl)thiomethyl-3-cephem-4-carboxylic acid trifluoroacetic acid salt (150 mg) was suspended in ethyl acetate (7.5 ml). To the suspension was added at 0° C. with stirring N,O-bis(trimethylsilyl)-acetamide (417 μl), and after stirring for 15 minutes at 0° C., there was added the acid chloride (78.2 mg) obtained above (Item a), and the mixture was stirred at 0° C. for one and half hours. To the reaction solution was added ethyl acetate (100 ml) and the mixture was successively washed with 20 ml each of 0.5 N hydrochloric acid, distilled water (twice) and a saturated aqueous solution of sodium chloride. Organic layer separated out was recovered and dried over magnesium sulfate. The solvent was removed by distillation and the residue was dissolved in acetone (15 ml), and allowed to stand overnight. The solvent was removed by distillation and the residue was triturated with ethyl ether. The precipitates thus formed were recovered by filtration, to obtaine the crude product (150 mg). The product was purified through a thin layer silica gel chromatography to obtain the desired product (79 mg).

Melting Point: 175°-185° C. (decomposition) Elemental analysis: for $C_{33}H_{29}N_7O_{13}S_2$,

|  | C | H | N |
|---|---|---|---|
| Calculated (%) | 49.81 | 3.67 | 12.32 |
| Found (%) | 48.25 | 3.58 | 11.20 |

Infrared absorption spectrum, (cm$^{-1}$, Nujol): 1770-1790, 1715, 1670, 1620
NMR spectrum, (δ, DMSO-d$_6$);
2.34(3H, s), 2.36(3H, s),
3.40(3H, s), 3.34(1H, d, J=18 Hz),
3.66(1H, d, J=18 Hz), 3.90(3H, s),
4.12(1H, d, J=13 Hz), 5.06(1H, s),
5.68(1H, d, J=8 Hz), 6.73(2H, d, J=8.5 Hz),
7.30(2H, d, J=8.5 Hz), 7.86(1H, s),
8.02(1H, s), 9.03(1H, s)

EXAMPLE 2

7β-[D-2-(7,8-Diacetoxychromone-3-carboxyamino)-2-(4-hydroxy phenyl)acetamido]-7α-methoxy-3-(1-methyl-5-tetrazolyl)thiomethyl-3-cephem-4-carboxylic acid (a) 7,8-Diacetoxychromone-3-carbonyl chloride A mixture of 7,8-diacetoxychromone-3-carboxylic acid (9.5 g), thionyl chloride (2.6 ml), dimethylformamide (0.1 ml) and benzene (300 ml) was refluxed for one and half hours, and there were further added thionyl chloride (2.6 ml) and dimethyl formamide (0.1 ml). The whole was then refluxed for further one hour. Then the solvent was removed therefrom by distillation, and the residue was triturated with n-hexane. The solid matter thus obtained was collected by filtration. There was thus obtained the desired product (9.3 g).

Infrared absorption spectrum, (cm$^{-1}$, Nujol): 1780, 1770, 1670, 1620

(b) 7β-[D-2-(7,8-Diacetoxychromone-3-carboxamido)-2-(4-hydroxyphenyl)acetamido]-7α-methoxy-3-(1-methyl-5-tetrazolyl)thiomethyl]-3-cephem-4-carboxylic acid 7β-[D-2-Amino-2-(4-hydroxyphenyl)acetamido]-7α-methoxy-3-(1-methyl-5-tetrazolyl)thiomethyl-3-cephem-4-carboxylic acid trifluoroacetic acid salt (150 mg) was suspended in ethyl acetate (7.5 ml), and was added thereto N,O-bis(trimethylsilyl)-acetamide (417 μl) at 0° C. with stirring. To the resulting mixture was added the acid chloride (78.2 mg) which was obtained above (Item a), and the whole was stirred at 0° C. for three hours. The reaction solution, after addition thereto of ethyl acetate (100 ml), was successively washed with 20 ml each of 0.5 N hydrochloric acid, distilled water (twice) and a saturated aqueous solution of sodium chloride. The organic layer was dried over magnesium sulfate. The residue remained, after the solvent was removed therefrom by distillation, was dissolved in acetone (15 ml), and the solution was allowed to stand overnight at room temperature. The solvent was distilled off from the solution, and the residue was triturated with ethyl ether to give crude product (98 mg), which was washed with a mixture of ethyl ether, acetone and methanol in the proportion by volume of 9:0.5:0.5 to obtain the desired product (69 mg).

Melting Point: 175°-190° C. Elemental analysis: for $C_{33}H_{29}N_7O_{13}S_2$.

|  | C | H | N |
|---|---|---|---|
| Calculated (%) | 49.81 | 3.67 | 12.32 |
| Found (%) | 49.24 | 3.89 | 10.29 |

Infrared absorption spectrum, (cm$^{-1}$, Nujol): 1770-1790, 1715, 1670, 1615
NMR spectrum, (δ, DMSO-d$_6$):
2.37(3H, s), 2.43(3H, s),
3.40(3H, s), 3.6(2H, br),
3.89(3H, s), 4.16(1H, d, J=13 Hz),
4.36(1H, d, J=13 Hz), 5.06(1H, s),
5.67(1H, d, J=8 Hz), 6.73(2H, d, J=8.5 Hz),
7.30(2H, d, J=8.5 Hz), 7.55(1H, d, J=9 Hz),
8.10(1H, d, J=9 Hz), 8.99(1H, s)

EXAMPLE 3

7β-[D-2-(6,7-Dihydroxychromone-3-carboxyamido)-2-(4-hydroxyphenyl)acetamido]-7α-methoxy-3-(1-methyl-5-tetrazolyl)thiomethyl-3-cephem-4-carboxylic acid (a) 6,7-Dihydroxychromone-3-carbonyl chloride 6,7-Dihydroxychromon-3-carboxylic acid (888 mg) together with thionyl chloride (25 ml) were refluxed for one hour. Any unreacted thionyl chloride was then removed from the reaction mixture by distillation. Benzene was added to the residue, and the mixture was subjected to distillation. The residue was triturated with dichloromethane to obtain the desired product (719 mg).

Infrared absorption spectrums, (cm$^{-1}$, Nujol): 1780, 1765, 1645, 1625

(b) 7β-[D-2-(6,7-Dihydroxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-Amino-2-(4-hydroxyphenyl)acetamido]-7α-methoxy-3-(1-methyl-5-tetrazolyl)thiomethyl-3-cephem-4-carboxylic acid trifluoroacetic acid salt (150 mg) was subjected to suspension into ethyl acetate (7.5 ml) and was added thereto with stirring at 0° C. N,O-bis(trimethylsilyl)acetamide (417 μl). To the resulting mixture was added with stirring at 0° C. dihydroxychromon-3-carbonyl chloride (58 mg) which was obtained in the preceding Item (a). There was added once more N,O-bis(trimethylsilyl)acetamide (417 μl), and the whole was stirred at 0° C. for three hours. After addition of ethyl acetate (150 ml) to the reaction solution, the mixture was washed successively with 30 ml each of 0.5 N hydrochloric acid, distilled water (twice) and a saturated saline. The organic layer recovered therefrom was dried over magnesium sulfate, and the solvent was distilled off. The residue thus obtained was dissolved in acetone (30 ml) and allowed to stand at room temperature overnight. After removal by filtration of a small quantity of an insoluble matter separated out, the solvent was distilled off. Ethyl ether was added to the residue to cause trituration of the latter. There was thus obtained through filtration the desired substance (105 mg).

Melting Point: 160°–185° C. (decomposition) Elemental analysis: for $C_{29}H_{25}N_7O_{11}S_2$,

|  | C | H | N |
|---|---|---|---|
| Calculated (%) | 48.94 | 3.54 | 13.78 |
| Found (%) | 46.42 | 3.38 | 10.38 |

Infrared absorption spectrum, ($cm^{-1}$, Nujol); 1770–1780, 1710, 1665, 1615,
NMR spectrum, (δ, DMSO-$d_6$):
3.40(3H, s), 3.89(3H, s),
4.11(1H, d, J=13 Hz), 4.34(1H, d, J=13 Hz),
5.04(1H, s), 5.64(1H, d J=8 Hz),
6.73(2H, d, J=8.5 Hz), 6.97(1H, s),
7.29(2H, d, J=8.5 Hz), 7.39(1H, s),
8.85(1H, s),

EXAMPLE 4

7β-[D-2-(7,8-Dihydroxychromone-3-carboxyamido)-2-(4-hydroxyphenyl)acetamido]-7α-methoxy-3-(1-methyl-5-tetrazolyl)thiomethyl-3-cephem-4-carboxylic acid (a) 7,8-Dihydroxychromone-3-carbonyl chloride 7,8-Dihydroxychromone-3-carboxylic acid (6.6 g) together with thionyl chloride (25 ml) were refluxed for one hour. Certain unreacted thionyl chloride remained in the reaction mixture was distilled off, and after addition of benzene to the residue, the mixture was again subjected to distillation. To the residue was added n-hexane to cause trituration of the residue. The solid matter thus formed was recovered by filtration. There was thus obtained the desired product (7.2 g).

Infrared absorption spectrum ($cm^{-1}$, Nujol): 1775, 1660, 1620

(b) 7β-[D-2-(7,8-Dihydroxychromone-3-carboxamido)-2-(4-hydroxyphenyl)acetamido]-7α-methoxy-3-(1-methyl-5-tetrazolyl)thiomethyl-3-cephem-4-carboxylic acid 7β-[D-2-Amino-2-(4-hydroxyphenyl)acetamido]-7α-methoxy-3-(1-methyl-5-tetrazolyl)thiomethyl-3-cephem-4-carboxylic acid trifluoroacetic acid salt (150 mg) as subjected to suspension into ethyl acetate (7.5 ml). To the suspension was added at 0° C. and with stirring N,O-bis(trimethyl-silyl)acetamide (417 μl), and to the resulting mixture was added with stirring at 0° C. 7,8-dihydroxychromone-3-carbonyl chloride (58 mg) which was obtained in the preceding paragraphs of (Item a). There was further added N,O-bis(-trimethyl-silyl)acetamide (417 μl), and the whole was stirred at 0° C. for 3 hours. To the reaction solution was added ethyl acetate (150 ml). The mixture was successively washed with 30 ml each of 0.5 N hydrochloric acid, distilled water (twice) and a saturated saline. The organic layer recovered was dried over magnesium sulfate, and the solvent was then removed therefrom by distillation. The residue was dissolved in acetone (30 ml) and the solution was allowed to stand at room temperature overnight. A small quantity of the separated insoluble substance was removed by filtration, and the solvent was distilled off from the filtrate. The residual substance was triturated with ethyl ether. There was thus obtained the crude product (88 mg). The latter was dissolved in a mixture of ethyl ether, acetone and methanol in proportion of 1:1:1 by volume. After removal of the insoluble matter by filtration, the filtrate was concentrated and the residual matter was triturated with ethyl ether. The resulting solid matter was washed with a mixture of ethyl ether, acetone and methanol in proportion by volume of 8:1:1. There was thus obtained the desired product (21 mg).

Melting Point: 170°–200° C. (decomposition) Elemental analysis: for $C_{29}H_{25}N_7O_{11}S_2$

|  | C | H | N |
|---|---|---|---|
| Calculated (%) | 48.94 | 3.54 | 13.78 |
| Found (%) | 43.08 | 3.26 | 9.03 |

Infrared absorption spectrum, ($cm^{-1}$ Nujol); 1770–1780, 1710, 1665, 1615
NMR spectrums, (δ, DMSO-$d_6$);
3.40(3H, s), 3.90(3H, s),
4.13(1H, d, J=13 Hz), 4.34(1H, d, J=13 Hz),
5.05(1H, s), 5.64(1H, d, J=7 Hz),
6.73(2H, d, J=8.5 Hz), 7.04(1H, d, J=9 Hz),
7.30(2H, d, J=8.5 Hz), 7.51(1H, d, J=9 Hz),
8.91(1H, s).

EXAMPLE 5

7β-[D-2-(6,7-Dihydroxychromone-3-carboxamido)-2-phenylacetamido]-7α-methoxy-3-acetoxymethyl-3-cephem-4-carboxylic acid and sodium salt thereof (a) 7β-[D-2-(6,7-Dihydroxychromone-3-carboxamido)-2-phenylacetamido]-7α-methoxy-3-acetoxymethyl-3-cephem-4-carboxylic acid 7β-(D-2-Amino-2-phenylacetamido)-7α-methoxy-3-acetoxymethyl-3-cephem-4-carboxylic acid trifluoro acetic acid salt (700 mg) was suspended in ethyl acetate (35 ml). To the suspension was added at 0° C. with stirring N,O-bis(trimethylsilyl)acetamide (2.20 ml). at 10 minutes' lapse, there was added 6.7-dihydroxychromon-3-carbonyl chloride (305.5 mg) obtained above (Item a) of Example (3). The mixture was stirred for one hour at 0° C. and then two hours at 15° C.

Ethyl acetate (700 ml) was added to the reaction mixture, and the whole was successively washed with 140 ml each of 0.5 N hydrochloric acid, distilled water (twice) and a saturated aqueous solution of sodium chloride. The organic layer separated out was recovered and dried over magnesium sulfate. The solvent was then distilled off therefrom and the residue was dissolved in acetone (70 ml) and the solution was allowed to stand at room temperature overnight. The solvent was distilled off from the solution, and the residue was triturated with ethyl ether. The solid mass was washed with a mixture of ethyl ether, acetone and methanol in the ratio of 9:0.5:0.5 by volume. There was thus obtained the desired product (181 mg).

Melting Point: 200°-250° C. (decomposition) Elemental analysis: for $C_{29}H_{25}N_3O_{12}S$,

|  | C | H | N |
|---|---|---|---|
| Calculated (%) | 54.46 | 3.94 | 6.57 |
| Found (%) | 48.85 | 3.73 | 6.83 |

Infrared absorption spectrums (cm$^{-1}$, Nujol); 1780, 1730, 1710, 1665, 1635
NMR spectrums, (δ, DMSO-d$_6$);
2.00(3H, s), 3.18(1H, d, J=18 Hz),
3.41(3H, s), 3.52(1H, d, J=18 Hz),
4.60(1H, d, J=13 Hz), 4.90(1H, d, J=13 Hz),
5.11(1H, s), 5.81(1H, d, J=7.5 Hz),
6.98(1H, s), 7.1-7.6(5H, m),
7.40(1H, s), 8.86(1H, s), (b) Sodium salt of the said carboxylic acid obtained in the preceding paragraphs under Item (a)

The said carboxylic acid (30 mg) obtained in Item (a) was dissolved in tetrahydrofuran (1.2 ml). To the solution was added with stirring 0.5 M solution of sodium 2-ethylhexanoate (94 μl) in tetrahydrofuran. Precipitate formed was recovered by filtration and washed with tetrahydrofuran. There was thus, obtained the desired product (24 mg).

Melting Point: 200°-230° C. (decomposition) Elemental Analysis: for $C_{29}H_{24}N_3NaO_{12}S$

|  | C | H | N |
|---|---|---|---|
| Calculated (%) | 52.65 | 3.66 | 6.35 |
| Found (%) | 48.84 | 3.56 | 5.60 |

Infrared absorption spectrum, (cm$^{-1}$, Nujol): 1765, 1730, 1665, 1610-1630
NMR spectrum (δ DMSO-d$_6$):
1.99(3H, s), 2.96(1H, d, J=17 Hz),
3.43(3H, s), 3.50(1H, d, J=17 Hz),
4.67(1H, d, J=12 Hz), 4.86(1H, d, J=12 Hz),
4.95(1H, s), 5.86(1H, d, J=7.5 Hz),
6.97(1H, s), 7.37(1H, s),
7.1-7.7(5H, m), 8.83(1H, s).

(c) Disodium salt of the compound obtained in the preceding Item (a), i.e., sodium salt of 7β-[D-2-(6-hydroxy-7-sodio-oxychromone-3-carboxamido)-2-phenylacetamido]-7α-methoxy-3-acetoxymethyl-3-cephem-4-carboxylic acid The compound (30 mg) formed in the preceding Item (a) were dissolved in 0.6 ml of dimethylformamide (0.6 ml). To the solution thus formed was added with stirring a 0.5 M solution (282 μl) of sodium 2-ethyl hexanoate in dimethylformamide. The resulting solution was introduced drop wise with stirring into 7 ml of ethyl acetate. The precipitate thus formed was recovered by filtration and washed with ethyl acetate. There was thus obtained the desired product (20 mg).

Melting Point: 200°-230° C. (decomposition) Elemental analysis: for $C_{29}H_{28}N_3Na_2O_{12}S$

|  | C | H | N |
|---|---|---|---|
| Calculated (%): | 50.95 | 3.39 | 6.15 |
| Found (%): | 47.17 | 3.78 | 5.34 |

Infrared absorption spectrum, (cm$^{-1}$, Nujol): 1765, 1730, 1665, 1610-1630
NMR spectrums (δ, DMSO-d$_6$):
1.98(3H, s), 2.92(1H, d, J=17 Hz),
3.38(1H, d, J=17 Hz), 3.42(1H, s),
4.68(1H, d J=12 Hz), 4.82(1H, d, J=12 Hz),
4.92(1H, s), 5.84(1H, d, J=8 Hz),
6.04(1H, s), 6.94(1H, s),
7.2-7.7(5H, m), 8.54(1H, s)

EXAMPLE 6

7β-[D-2-(6,7-Dihydroxychromone-3-carboxyamido)-2-phenylacetamido]-7α-methoxy-3-[2-5-methyl-2-(1,3,4-thiadiazolyl)]thiomethyl-3-cepnem-4-carboxylic acid The compound (100 mg) obtained in Item (a) of the preceding Example 5 and 2-mercapto-5-methyl-1,3,4-thiadiazol (87 mg) were dissolved in 2.5 ml of dimethylformamide (2.5 ml). To the solution thus obtained were added dropwise at 65° C. with stirring a mixture of hydrogen sodium carbonate (83 mg), distilled water (2.5 ml) and a phosphoric acid buffer solution (5 ml). The whole was stirred at 65° C. for further 12 hours, cooled with ice and filtered. To the filtrate was added distilled water (15 ml) and 1.5 1 N hydrochloric acid (1.5 ml). The precipitate separated out was collected by filtration and washed successively with distilled water, isopropanol and ethanol to obtain the desired product.

Apart from the above, the solvents or the spent washings recovered, i.e., isopropanol and ethanol were distilled off. The residue collected was triturated with a mixture of ethyl ether and ethanol in proportion of 4:1 by volume, and washed with ethyl ether in order to recover an additional amount of the desired product.

There was thus obtained in total the combined product (30.4 mg).

Melting Point: 188°-190° C. (decomposition) Elemental analysis: for $C_{30}H_{23}N_5O_{10}S_3$,

|  | C | H | N |
|---|---|---|---|
| Calculated (%): | 50.63 | 3.54 | 9.84 |
| Found (%): | 49.12 | 3.88 | 8.51 |

Infrared absorption spectrum, (cm$^{-1}$, Nujol): 1770, 1660, 1610, 1520
NMR spectrum (δ, DMSO-d$_6$):
2.69(3H, s), 3.23(1H, d, J=18 Hz),
3.42(3H, s), 3.61(1H, d, J=13 Hz),
4.13(1H, d, J=13 Hz), 4.50(1H, d, J=13 Hz),
5.09(1H, s), 5.83(1H, d, J=8 Hz),
6.99(1H, s), 7.20-7.60(5H, m),
7.42(1H, s), 8.87(1H, s), The compounds described in the following Examples 7-13 were also obtained in accordance with the methods similar to those disclosed in the above Examples 1-6:

EXAMPLE 7

7β-[D-2-(7,8-Dihydroxychromone-3-carboxyamido)-2-phenylacetamido]-7α-methoxy-3-acetoxymethyl-3-cephem-4-carboxylic acid Yield: 18% Melting Point: 200°-240° C. (decomposition) Elemental analysis: for $C_{29}H_{25}N_3O_{12}S$,

|  | C | H | N |
|---|---|---|---|
| Calculated (%): | 54.46 | 3.94 | 6.57 |
| Found (%): | 53.75 | 4.01 | 6.23 |

Infrared absorption spectrum, (cm$^{-1}$, Nujol): 1775, 1735, 1715, 1670, 1620

NMR spectrum, (δ, DMSO-d$_6$):
2.00(3H, s), 3.19(1H, d, J=18 Hz)
3.42(3H, s), 3.52(1H, d, J=18 Hz),
4.61(1H, d, J=13 Hz), 4.88(1H, d, J=18 Hz),
5.11(1H, s), 5.81(1H, d, J=7.5 Hz),
7.03(1H, d, J=8.5 Hz), 7.1–7.6(6H, m),
8.93(1H, s).

EXAMPLE 8

7β-[D-2-(5-Methoxychromone-3-carboxyamido)-2-(4-hydroxyphenyl)acetamido]-7α-methoxy-3-(1-methyl-5-tetrazolyl)thiomethyl-3-cephem-4-carboxylic acid Yield: 57% Melting Point: 170°–195° C. (decomposition) Elemental analysis: for C$_{30}$H$_{27}$N$_7$O$_{10}$S$_2$

|  | C | H | N |
|---|---|---|---|
| Calculated (%): | 50.77 | 3.83 | 13.82 |
| Found (%): | 48.78 | 3.96 | 11.13 |

Infrared absorption spectrum, (cm$^{-1}$, Nujol): 1770, 1730, 1670, 1620

NMR spectrum, (δ, DMSO-d$_6$):
3.40(3H, s), 3.90(6H, s),
4.10(1H, d, J=13 Hz), 4.36(1H, d, J=13 Hz),
5.07(1H, s), 5.64(1H, d, J=7.5 Hz),
6.75(2H, d, J=8.5 Hz), 7.08(1H, d, J=8 Hz),
7.20(1H, d, J=8 Hz), 7.30(2H, d, J=8.5 Hz),
7.76(1H, t, J=8 Hz), 8.85(1H, s).

EXAMPLE 9

Sodium salt of 7β-[D-2-(5-methoxychromone-3-carboxyamido)-2-(4-hydroxyphenyl)acetamido]-7α-methoxy-3-(1-methyl-5-tetrazolyl)thiomethyl-3-cephem-4-carboxylic acid Yield: 88% Melting Point: 200°–230° C. (decomposition) Elemental analysis: C$_{30}$H$_{26}$N$_7$NaO$_{10}$S$_2$

|  | C | H | N |
|---|---|---|---|
| Calculated (%): | 49.24 | 3.58 | 13.40 |
| Found (%): | 49.01 | 3.64 | 12.56 |

Infrared absorption spectrum, (cm$^{-1}$, Nujol): 1760, 1670, 1610

NMR spectrum, (δ, DMSO-d$_6$):
3.41(3H, s), 3.89(3H, s),
3.91(3H, s), 4.25(2H, br.s),
4.88(1H, s), 5.68(1H, d, J=7 Hz),
6.75(2H, d, J=8.5 Hz), 7.09(1H, d, J=8 Hz),
7.21(1H, d, J=8 Hz), 7.30(2H, d, J=8.5 Hz),
7.77(1H, t, J=8 Hz), 8.85(1H, s).

EXAMPLE 10

7β-[D-2-(Chromone-3-carboxamido)-2-(4-hydroxyphenyl)acetamido]-7α-methoxy-3-(1-methyl-5-tetrazolyl)thiomethyl-3-cephem-4-carboxylic acid Yield: 34% Melting Point: 175°–200° C., (decomposition) Elemental analysis: for C$_{29}$H$_{25}$N$_7$O$_9$S$_2$,

|  | C | H | N |
|---|---|---|---|
| Calculated (%): | 51.24 | 3.71 | 14.43 |
| Found (%): | 49.12 | 3.90 | 11.62 |

Infrared absorption spectrum, (cm$^{-1}$, Nujol): 1770–1790, 1710, 1665, 1615

NMR spectrums, (δ, DMSO-d$_6$):
3.40(3H, s), 3.90(3H, s),
4.13(1H, d, J=13 Hz), 4.36(1H, d, J=13 Hz)
5.06(1H, s), 5.68(1H, d, J=7 Hz),
6.75(2H, d, J=8.5 Hz), 7.31(2H, d, J=8.5 Hz),
7.4–8.1(3H, m), 8.18(1H, br. d, J=8 Hz),
9.04(1H, s).

EXAMPLE 11

7β-[D-2-(6-Nitrochromone-3-carboxamido)-2-phenylacetamido]-7α-methoxy-3-acetoxymethyl-3-cephem-4-carboxylic acid Yield: 56%

Melting Point: 140°–150° C. (decomposition) Elemental analysis: for C$_{28}$H$_{24}$N$_4$O$_{12}$S,

|  | C | H | N |
|---|---|---|---|
| Calculated (%): | 52.50 | 3.78 | 8.75 |
| Found (%): | 52.01 | 3.92 | 8.62 |

Infrared absorption spectrums, (cm$^{-1}$, Nujol): 1775, 1740, 1720, 1670, 1620

NMR spectrum (δ, DMSO-d$_6$):
2.00(3H, s), 3.21(1H, d, J=18 Hz),
3.43(3H, s), 3.54(1H, d, J=18 Hz),
4.63(1H, d, J=13 Hz), 4.92(1H, d, J=13 Hz),
5.14(1H, s), 5.86(1H, d, J=7.5 Hz),
7.2–7.7(5H, m), 8.05(1H, d, J=9 Hz),
8.66(1H, dd, J=9 Hz, 2.5 Hz),
8.87(1H, d, J=25 Hz), 9.13(1H, s),

EXAMPLE 12

7β-[D-2-(7-Chlorochromone-3-carboxyamido)-2-phenylacetamido]-7α-methoxy-3-acetoxymethyl-3-cephem-4-carboxylic acid Yield: 41% Melting Point: 150°–165° C. (decomposition) Elemental analysis: for C$_{29}$H$_{24}$ClN$_3$O$_{10}$S

|  | C | H | N |
|---|---|---|---|
| Calculated (%): | 54.25 | 3.77 | 6.55 |
| Found (%): | 53.63 | 3.73 | 6.53 |

Infrared absorption spectrum (cm$^{-1}$, Nujol): 1770–1790, 1730, 1710, 1700, 1670, 1605

NMR spectrum, (δ, DMSO-d$_6$):
2.01(3H, s), 3.21(1H, d, J=18 Hz),
3.44(3H, s), 3.53(1H, d, J=18 Hz),
4.64(1H, d, J=13 Hz), 4.92(1H, d, J=13 Hz),
5.13(1H, s), 5.84(1H, d, J=7.5 Hz),
7.1–7.9(6H, m), 8.02(1H, d, J=2 Hz),
8.20(1H, d, J=8.5 Hz), 9.05(1H, s)

EXAMPLE 13

7β-[D-2-(7-Benzyloxy-8-methylchromone-3-carboxamido)-2-phenylacetamido]-7α-methoxy-3-acetoxymethyl-3-cephem-4-carboxylic acid Yield: 46% Melting Point: 145°–170° C. (decomposition) Elemental analysis: for $C_{37}H_{33}N_2O_{11}S$,

|  | C | H | N |
|---|---|---|---|
| Calculated (%): | 61.06 | 4.57 | 5.77 |
| Found (%): | 60.28 | 4.48 | 5.70 |

Infrared absorption spectrums, (cm$^{-1}$, Nujol): 1780, 1740, 1725, 1705, 1665, 1615

NMR spectrums, (δ, DMSO-d$_6$):
2.01(3H, s), 2.34(3H, s),
3.21(1H, d, J=18 Hz), 3.44(3H, s),
3.54(1H, d, J=18 Hz), 4.64(1H, d, J=13 Hz)
4.92(1H, d, J=13 Hz), 5.13(1H, s),
5.36(2H, s), 5.84(1H, d, J=7.5 Hz),
7.2–7.7(11H, m), 9.03(1H, s),

EXAMPLE 14

7β-[D-2-(6,7-Dihydroxychromone-3-carboxamido)-2-(4-hydroxyphenyl)acetamido]-7α-methoxy-3-acetoxymethyl-3-cephem-4-carboxylic acid 7β-[D-2-Amino-2-(4-hydroxyphenyl)acetamido]-7α-methoxy-3-acetoxymethyl-3-cephem-4-carboxylic acid trifluoroacetic acid salt (680 mg) was suspended in tetrahydrofuran (25 ml). Into the suspension was added N,O-bis(trimethylsilyl)acetamide (1.33 ml), and the mixture was stirred at 0° C. After 10 minutes, 6,7-dihydroxychromone-3-carbonylchloride (289 g) as mentioned in (a) of Example 3 was added into the suspension, and it was stirred for further two hours at the same temperature. The reaction mixture was concentrated to about 10 ml, and the concentrate was poured into 0.5 N hydrochloric acid (100 ml) at 0° C. The precipitate thereby formed was collected by filtration, and washed with water. It was dissolved in tetra-hydrofuran (100 ml), and the solution was dried over magnesium sulfate. After the solution was concentrated to about 10 ml, it was poured into ethyl ether (100 ml). The precipitate thereby formed was collected by filtration, and dired to yield the desired product (294 mg). The solvent was removed from the filtrate by distillation, and tetrahydrofurn and ethyl ether (0.2:9.8) were added into the residue for trituration, whereby the desired product (102 mg) were obtained, thereby making a total of the desired porduct (396 mg).

Melting Point: Ca. 250° C. (decomposition). Elemental analysis: for $C_{33}H_{25}N_3O_{13}S$

|  | C | H | N |
|---|---|---|---|
| Calculated (%): | 56.33 | 3.58 | 5.97 |
| Found (%): | 51.78 | 3.90 | 6.22 |

Infrared absorption spectrum (cm$^{-1}$, nujol): 1770, 1720, 1710, 1615–1650.

NMR spectrum (δ, DMSO-d$_6$):
2.01(3H, s), 3.21(1H, br. d, J=18 Hz)
3.42(3H, s), 3.54(1H, br. d, J=18 Hz),
4.62(1H, d, J=13 Hz), 4.90(1H, d, J=13 Hz),
5.10(1H, s), 5.67(1H, d, J=7.5 Hz),
6.74(2H, d, J=9 Hz), 6.98(1H, s),
7.31(2H, d, J=9 Hz), 7.40(1H, s),
8.86(1H, s)

EXAMPLE 15

7β-[D-2-(6,7-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid The compound (250 mg) obtained as described in Example 14 and 5-mercapto-1-carboxymethyl-tetrazole (85.3 mg) were dissolved in dimethylformamide (15 ml). Sodium hydrogen carbonate (149 mg) was dissolved in a potassium phosphate buffer solution (10 ml) (0.1 M, pH 6.4), and the resulting solution was added dropwise into the above solution at 70° C. over 45 minutes while it was being stirred. The mixture was further stirred for 4.5 hours at the same temperature. Then, the reaction mixture was cooled to room temperature, and added into dilute hydrochloric acid (5 ml of 1 N hydrochloric acid+100 ml of water) at 0° C. while it was being stirred. The resulting precipitate was collected by filtration, and after it was washed with ethyl ether, it was dissolved in tetrahydrofuran (50 ml), and dried over magnesium sulfate. Then, the solution was concentrated to about 6 ml, and the concentrate was added into ethyl ether (100 ml) while it was being stirred. The resulting precipitate was collected by filtration, washed with ethyl ether, and dired to yield the desired product (124 mg).

Melting Point: 230° C.–250° C. (decomposition). Elemental analysis: for $C_{30}H_{25}N_7O_{13}S_2$

|  | C | H | N |
|---|---|---|---|
| Calculated (%): | 47.68 | 3.33 | 12.98 |
| Found (%): | 46.52 | 3.27 | 11.07 |

Infrared absorption spectrum (cm$^{-1}$, nujol): 1765–1775, 1730, 1660, 1610,

NMR spectrum (δ, DMSO-d$_6$)
3.42(3H, s), 3.6(2H, br),
4.10(1H, d, J=14 Hz), 4.50(1H, d, J=14 Hz),
5.01(1H, s), 5.29(2H, br, s),
5.68(1H, d, J=8 Hz), 6.74(2H, d, J=8 Hz),
6.99(1H, s), 7.31(2H, d, J=8 Hz),
7.40(1H, s), 8.87(1H, s)

EXAMPLE 16

7β-[D-2-(6,7-Dihydroxychromone-3-carboxamido)-2-(4-hydroxyphenyl)acetamido]-7α-methoxy-3-1-carboxymethyl-5-tetrazolyl)thiomethyl-3-cephem-4-carboxylic acid disodium salt The compound (26.6 mg) obtained in Example 15 was dissolved in 0.6 ml of methanol-tetrahydrofuran (1:1), and 70.2 μl of a 0.5 M methanol solution of sodium 2-ethylhexanoate was added thereinto while it was being stirred. Then, ethyl acetate (6 ml) was added to the reaction mixture, and the resulting precipitate was collected by filtration. The precipitate was washed with ethyl acetate, and then ethyl ether, and dried to yield the desired product (19.0 mg).

Melting Point: Ca. 250° C. (decomposition) Elemental analysis: for $C_{30}H_{23}N_7O_{13}S_2Na_2$

|  | C | H | N |
|---|---|---|---|
| Calculated (%): | 45.06 | 2.90 | 12.26 |

-continued

| | C | H | N |
|---|---|---|---|
| Found (%): | 44.55 | 2.86 | 11.88 |

Infrared absorption spectrum (cm$^{-1}$, nujol): 1750–1775, 1660, 1600–1625.
NMR spectrum (δ, DMSO-d$_6$):
3.41(3H, s), 4.25(2H, br),
4.66(2H, br, s), 4.91(1H, s),
5.67(1H, d, J=7.5 Hz), 6.75(2H, d, J=8.5 Hz),
7.03(1H, s), 7.30(2H, d, J=8.5 Hz),
7.42(1H, s), 8.84(1H, s)

EXAMPLE 17

7β-[D-2-(7,8-Dihydroxychromone-3-carboxamido)-2-(4-hydroxyphenyl)acetamido]-7α-methoxy-3-acetoxymethyl-3-cephem-4-carboxylic acid 7β-[D-2-Amino-2-(4-hydroxyphenyl)acetamido]-7α-methoxy-3-acetoxymethyl-3-cephem-4-carboxylic acid trifluoroacetic acid salt (230 mg) was suspended in tetrahydrofuran (7 mg), and N,O-bis(trimethylsilyl)acetamide (454 μl) was added to the suspension at 0° C. while it was being stirred. After 10 minutes, the acid chloride (98 mg) obtained in (a) of Example 4 was added, and stirring was continued for further two hours at the same temperature. The reaction mixture was concentrated to about 3 ml, and the concentrate was added into 0.5 N hydrochloric acid (30 ml) at 0° C. The resulting precipitate was collected by filtration, washed with water, and dried. The power thus obtained was washed with tetrahydrofuran-ethyl ether (0.2:9.8) and then with ethyl ether, and dried to yield the desired product (153 mg).

Melting Point: 220° C.–260° C. (decomposition). Elemental analysis: for C$_{33}$H$_{25}$N$_3$O$_{13}$S

| | C | H | N |
|---|---|---|---|
| Calculated (%): | 56.33 | 3.58 | 5.97 |
| Found (%): | 55.91 | 3.52 | 5.67 |

Infrared absorption spectrum (cm$^{-1}$, nujol): 1770, 1725, 1710, 1660, 1615.
NMR spectrum (δ, DMSO-d$_6$):
2.00(3H, s), 3.42(3H, s),
4.61(1H, d, J=13 Hz), 4.90(1H, d, J=13 Hz),
5.09(1H, s), 5.66(1H, d, J=7.5 Hz),
6.73(2H, d, J=8.5 Hz), 7.04(1H, d, J=8.5 Hz),
7.30(2H, d, J=8.5 Hz), 7.51(1H, d, J=8.5 Hz)

EXAMPLE 18

7β-[D-2-(7,8-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid The compound (100 mg) obtained in Example 17 and 5-mercapto-1-carboxymethyltetrazole (34 mg) were suspended in dimethylformamide (2 ml). A solution obtained by dissolving sodium hydrogencarbonate (60 mg) in 4 ml of a potassium phosphate buffer solution (0.1 M, pH 6.4) was added dropwise to the above solution at 70° C. over 30 minutes while it was being stirred. Stirring was further continued for further five hours at the same temperature. The reaction mixture was cooled to room temperature, and added to dilute hydrochloric acid (2 ml of 1 N hydrochloric acid+40 ml of water) at 0° C. while it was being stirred. The resulting precipitate was collected by filtration, and washed with water. The precipitate was dissolved in tetrahydrofuran (20 ml), and dried over magnesium sulfate. Then, the solution was concentrated to about 3 ml, and the concentrate was added to ethyl ether (30 ml) while it was being stirred. The resulting precipitate was collected by filtration, and dried to yield the desired product (16 mg).

Melting Point: 220° C.–240° C. (decomposition). Elemental analysis: for C$_{30}$H$_{25}$N$_7$O$_{13}$S$_2$

| | C | H | N |
|---|---|---|---|
| Calculated (%): | 47.68 | 3.33 | 12.98 |
| Found (%): | 46.89 | 3.29 | 12.26 |

Infrared absorption spectrum (cm$^{-1}$, nujol): 1770, 1725, 1710, 1660, 1610.
NMR spectrum (δ, DMSO-d$_6$):
3.42(3H, s), 5.01(1H, s),
5.28(2H, br, s), 5.68(1H, d, J=7.5 Hz),
6.74(2H, d, J=8.5 Hz), 7.04(1H, d, J=8.5 Hz),
7.30(2H, d, J=8.5 Hz), 7.52(1H, d, J=8.5 Hz),
8.91(1H, s)

EXAMPLE 19

7β-[D-2-(6,7-Dihydroxychromone-3-carboxamido)-2-(4-hydroxyphenyl)acetamido]-7α-methoxy-3-(1-methoxycarbonylmethyl-5-tetrazolyl)thiomethyl-3-cephem-4-carboxylic acid (a) 7β-[D-2-(t-Butoxycarboxamido)-2-[4-(2-tetrahydropyranyl)oxyphenyl]acetamido]-3-(1-methoxycarbonylmethyl-5-tetrazolyl)thiomethyl-3-cephem-4-carboxylic acid benzhydryl ester Lithium methoxide (133 mg) was dissolved in methanol (4 ml) and tetrahydrofuran (14 ml) at room temperature under argon, and the resulting solution was cooled to −74° C. 7β-[D-2-(t-Butoxycarboxamide)-2-[4-(2-tetrahydropyranyl)oxyphenyl]acetamide]-3-(1-carboxymethyl-5-tetrazolyl)thiomethyl-3-cephem-4-carboxylic acid dibenzhydryl ester (1.009 g) was dissolved in tetrahydrofuran (3.5 ml), and the resulting solution was added to the aforesaid lithium methoxide solution under argon while it was being stirred. They were reacted for 15 minutes, while the temperature was maintained at −74° C., followed by addition of acetic acid (1 ml). The reaction mixture was added to chloroform-(200 ml) a 5% aqueous solution (50 ml) of sodium hydrogencarbonate, and stirred therewith. The organic layer was washed with a 5% aqueous solution of sodium hydrogen carbonate, then water, and then a saturated aqueous solution of sodium chloride. It was dried over magnesium sulfate, and the solvent was removed by distillation. The residue was purified by silica gel column chromatography employing an elution solvent comprising ethyl acetate and benzene at a ratio of 15:85, whereby the desired product (549 mg) was obtained.

Infrared absorption spectrum (cm$^{-1}$, nujol): 1780, 1750, 1660–1720

(b) 7β-[D-2-(t-Butoxycarboxamido)-2-[4-(2-tetrahydropyranyl)oxyphenyl]acetamido]-7α-methoxy-3-(1-methoxycarbonylmethyl-5-tetrazolyl)thiomethyl-3-cephem-4-carboxylic acid benzhydryl ester Lithium methoxide (239 mg) was dissolved in methanol (7 ml) and tetrahydrofuran (14 ml) at room temperature under argon.

The compound (1.595 g) obtained in (a) above was dissolved in tetrahydrofuran (4.8 ml), and the solution was added over one minute under argon into the aforesaid lithium methoxide solution cooled to −75° C., while it was being stirred. Then, t-butyl hypochloride (279 μl) was added dropwise into the solution while it was being stirred. Stirring was continued for 15 minutes at −75° C., followed by addition of acetic acid (1.5 ml). The reaction mixture was added to chloroform (200 ml) and 50 ml of a 5% aqueous solution of sodium hydrogen carbonate. The organic layer was washed with a 5% aqueous solution of sodium hydrogen carbonate, then with a saturated aqueous solution of sodium chloride. It was dried over magnesium sulfate, and the solvent was removed by distillation. The residue was purified by silica gel column chromatography employing an elution solvent comprising ethyl acetate and benzene at a ratio of 20:80, whereby the desired product (872 mg) were obtained.

Infrared absorption spectrum (cm$^{-1}$, nujol): 1780, 1750, 1670-1720.

(c) 7β-[D-2-Amino-2-(4-hydroxyphenyl)acetamido]-7α-methoxy-3-(1-methoxycarbonylmethyl-5-tetrazolyl)thiomethyl-3-cephem-4-carboxylic acid trifluoroacetic acid The compound (150 mg) obtained in (b) above was added into a mixture of trifluoroacetic acid (2.5 ml) and anisole (1 ml) cooled to 0° C., while it was being stirred. Stirring was continued for four hours at 0° C., and the reaction mixture was added to 50 ml of ethyl ether-n-hexane (1:1) while it was being stirred. The resulting precipitate was collected by filtration, washed with ethyl ether, and dired to yield the desired product (118 mg).

Infrared absorption spectrum (cm$^{-1}$, nujol): 1760, 1705, 1690, 1675, 1640, 1610.

(d) 7β-[D-2-(6,7-Dihydroxychromone-3-carboxamido)-2-(4-hydroxyphenyl)acetamido]-7α-methoxy-3-(1-methoxycarbonylmethyl-5-tetrazolyl)thiomethyl-3-cephem-4-carboxylic acid The compound (21 mg) obtained in (c) above was suspended in tetrahydrofuran (1 ml), and N,O-bis(trimethylsilyl)acetamide was added into the suspension while it was being stirred. After 10 minutes of stirring, the acid chloride (7.5 mg) obtained in (a) of Example 3 was added, and stirring was continued for two more hours at 0° C. Then, the reaction mixture was added to 0.5 N hydrochloric acid (10 ml) at 0° C. The resulting precipitate was washed with water, and dried. The resulting power was washed with a mixture of tetrahydrofuran and ethyl ehter (0.2:9.8) and then with ethyl ether, and dired to yield the desired product (20 mg).

Melting Point: 200° C.-230° C. (decomposition) Elemental analysis: for C$_{31}$H$_{27}$N$_{7}$O$_{13}$S$_{2}$

|  | C | H | N |
|---|---|---|---|
| Calculated (%) | 48.37 | 3.54 | 12.74 |
| Found (%) | 48.42 | 3.48 | 12.56 |

Infrared absorption spectrum (cm$^{-1}$, nujol): 1765, 1720, 1705, 1660, 1615, 1605
NMR spectrum (δ, DMSO-d$_6$):
3.40(3H, s), 3.71(3H, s)
4.14(1H, d, J=12 Hz), 4.42(1H, d, J=12 Hz),
5.01(1H, s), 5.44(2H, br. s),
5.65(1H, d, J=8 Hz), 6.72(2H, d, J=8 Hz),
6.97(1H, s), 7.28(2H, d, J=8 Hz),
7.39(1H, s), 8.85(1H, s)

EXAMPLE 20

7β-[D-2-(6,7-Bis(ethoxycarbonyloxy)chromone-3-carboxamido)-2-(4-hydroxyphenyl)acetamido]7α-methoxy-3-(1-methoxycarbonylmethyl-5-tetrazolyl)thiomethyl-3-cephem-4-carboxylic acid (a) 6,7-Bis(ethoxycarbonyloxy)chromone-3-carbonyl chloride 6,7-Bis(ethoxycarbonyloxy)chromone-3-carboxylic cid (1.1 g) was dissolved in benzene (20 ml) and thionyl chloride (2 ml) was added dropwise at room temperature with stirring. Then, the mixture was refluxed with stirring. The reaction mixture was concentrated, and n-hexane was added to the concentrate to crystallize it. The resulting crystals were collected by filtration, washed with n-hexane and dired to afford the desired product (980 mg).

Melting Point: 89°-92° C.

(b) 7β-[D-2-(6,7-Bis(ethoxycarbonyloxy)chromone-3-carboxamido)-2-(4-hydroxyphenyl)acetamido]-7α-methoxy-3-(1-methoxycarbonylmethyl-5-tetrazolyl)thiomethyl-3-cephem-4-carboxylic acid The compound (34.0 mg) obtained in (c) of Example 19 was suspended in 1 ml of tetrahydrofuran (1 ml), and N,O-bis(trimethylsilyl)acetamide (56 μl) was added at 0° C. to the suspension while it was being stirred. After 10 minutes of stirring at 0° C., the acid chloride (19.2 mg) obtained at (a) were dissolved in tetrahydrofuran (1 ml), and stirring was further continued for further two hours at 0° C. Then, the reaction mixture was concentrated to 0.5 ml, and the concentrated solution was poured into 0.5 N ice-cooled hydrochloric acid (10 ml). The resulting precipitate was recovered by filtration and washed with water, and dried. The resulting material was dissolved in tetrahydrofuran (0.5 ml). The solution was added in ethylether (20 ml) with stirring. The resulting precipitate was recovered by filtration, and washed with 2% tetrahydrofuran-ethyl ether, and then ethyl ether, followed by drying to obtain 32 mg (yield: 73%) of the desired product.

Melting Point:140°-170° C. (decomposition) Infrared absorption spectrum (cm$^{-1}$, nujol): 1750-1790, 1665, 1610

NMR spectrum (δ, DMSO-d$_6$):
1.34(6H, t, J=7 Hz), 3.42(3H, s),
3.72(3H, s), 4.1-4.5(6H, m)
5.00 (1H, s), 5.40(2H, br. s),
5.66(1H, d, J=6.5 Hz), 6.72(2H, d, J=8 Hz),
7.29(2H, d, J=8 Hz), 7.99(1H, s),
8.14(1H, s), 9.03(1H, s)

EXAMPLE 21

Sodium salt of 7β-[D-2-(6,7-bis(ethoxycarbonyloxy)chromone-3-carboxyamido)-2-(4-hydroxyphenyl)-acetamido]-7α-methoxy-3-(1-methoxycarbonylmethyl-5-tetrazolyl)-thiomethyl-3-cephem-4-carboxylic acid The compound (13 mg) obtained in Example 20 was dissolved in a mixture (0.4 ml) of tetrahydrofuran and ethyl acetate in proportion of 1:1 by volume. To the solution was added 28 μl of a 0.5 m solution of sodium 2-ethylhexanoate in tetrahydrofuran and then ethyl ether (2 ml). The precipitate thus separated out was recovered by filtration, and washed with a mixture of ethyl acetate and ethyl ether in proportion of 1:1 by volume and with ethyl ether. After drying, there was obtained the desired product (12 mg).

Melting Point: 170°-21° C. (decomposition)
Infrared absorption spectrum, (cm$^{-1}$, Nujol): 1730–1790, 1660, 1615
NMR spectrums, ($\delta$, DMSO-d$_6$):
1.31(6H, t, J=7 Hz), 3.42(3H, s),
3.71(3H, s), 4.1–4.5(6H, m),
4.84(1H, s), 5.35(2H, br.s),
5.68(1H, d, J=7 Hz), 6.71(2H, d, J=8.5 Hz),
7.30(2H, d, J=8.5 Hz), 7.97(1H, s),
8.14(1H, s), 9.02(1H, s)

EXAMPLE 22

7$\beta$-[D-2-(6,7-Bis(ethoxycarbonyloxy)chromone-3-carboxamido)-2-(4-hydroxyphenyl)acetamido]-7$\alpha$-methoxy-3-acetoxymethyl-3-cephem-4-carboxylic acid 7$\beta$-[D-2-Amino-2-(4-hydroxyphenyl)acetamido]-7$\alpha$-methoxy-3-acetoxymethyl-3-cephem-4-carboxylic acid trifluoroacetic acid (226 mg) was suspended in tetrahydrofuran (7 ml). To the suspension was added with stirring at 0° C. N,O-bis(trimethylsilyl)acetamide (445 $\mu$l). After stirring for additional 10 minutes at 0° C., there was added to the mixture of 6,7-bis(ethoxycarbonyloxy)chromone-3-carbonyl chloride (154 mg) dissolved in tetrahydrofuran (4 ml), and the whole was stirred for two hours at room temperature. The reaction solution was concentrated to 3 ml, and the latter was poured into 0.5 N ice-cooled hydrochloric acid (30 ml). The precipitate separated out was recovered by filtration, washed with water, dried and washed successively with ethyl ether, a two % tetrahydrofuran solution in ethyl ether and again ethyl ether, followed by drying. There was thus obtained 261 mg of the product (82% yield).
Melting Point: 220° C. (decomposition)
Infrared absorption spectrum, (cm$^{-1}$, Nujol): 1760–1780, 1660–1680 and 1615
NMR spectrum ($\delta$, DMSO-d$_6$):
1.30(6H, t, J=7 Hz), 2.00(3H, s),
3.42(3H, s), 4.31(2H, q, J=7 Hz),
4.32(2H, q, J=7 Hz), 4.62(1H, d, J=13 Hz),
4.90(1H, d, J=13 Hz), 5.10(1H, s),
5.70(1H, d, J=7 Hz), 6.74(2H, d, J=7.5 Hz),
7.31(2H, d, J=7.5 Hz), 8.04(1H, s),
8.17(1H, s), 9.05(1H, s)

EXAMPLE 23

7$\beta$-[D-2-(6,7-Bis(2,2,2-trichloroethoxycarbonyloxy)-chromone-3-carboxamido)-2-(4-hydroxyphenyl)-acetamido]-7$\alpha$-methoxy-3-(1-methyl-5-tetrazolyl)-triomethyl-3-cephem-4-carboxylic acid (a) 6,7-Bis(2,2,2-trichloroethoxycarbonyloxy)chromone-3-carbonyl chloride 6.7-Bis(2,2,2-trichloroethoxycarbonyloxy)-chromone-3-carboxylic acid (57.3 mg) was dissolved in benzene (10 ml). To the solution was added with stirring at room temperature thionyl chloride (0.5 ml). The mixture was refluxed with stirring for three hours, and the reaction solution was concentrated. To the concentrate was added n-hexane (5 ml) to cause crystallization of the reaction product. The resulting product was recovered by filtration and washed with n-hexan and dried. There were thus obtained 34.8 ml of the desired product (34.8 mg).
Melting Point: 140°–142° C.
(b) 7$\beta$-[D-2-(6,7-Bis(2,2,2-trichloroethoxycarbonyloxy)chromone-3-carboxamido)-2-(4-hydroxyphenyl)-acetamido]-7$\alpha$-methoxy-3-(1-methyl-5-tetrazolyl)thiomethyl-3-cephem-4-carboxylic acid 7$\beta$-[D-2-Amino-2-(4-hydroxyphenyl)acetamido]-7$\alpha$-methoxy-3-(1-methyl-5-tetrazolyl)thiomethyl-3-cephem-4-carboxylic acid trifluoroacetic acid (62 mg) was suspended in of tetrahydrofuran (2 ml). To the suspension thus obtained were added at 0° C. with stirring N,O-bis(trimethylsilyl)acetamide (111 $\mu$l). The mixture was stirred at 0° C. for additional 10 minutes. A solution of the acid chloride (59.1 mg) obtained in the preceding paragraph under Item a), in 1 ml of tetrahydrofuran, was added to the above mixture, and the whole was stirred at 0° C. for two hours. The reaction solution was concentrated to 1 ml and poured into 20 ml of ice-cooled 0.5 N hydrochloric acid. Precipitate separated out was recovered by filtration, washed with water and dried. The dry substance was washed with a two % solution of tetrafuran in ethyl ether, followed by ethyl ether and again dried. There were obained 100 mg of the desired product (94% yield).
Melting Point: 170°–190° C. (decomposition) Elemental analysis: for C$_{35}$H$_{27}$Cl$_6$N$_7$O$_{15}$S$_2$

|  | C | H | N |
|---|---|---|---|
| Calculated (%) | 39.56 | 2.56 | 9.23 |
| Found (%) | 39.35 | 2.50 | 8.24 |

Infrared absorption spectrum (cm$^{-1}$, Nujol): 1740–1790, 1710, 1670, 1660, 1610
NMR spectrum, ($\delta$, DMSO-d$_6$):
3.41(3H, s), 3.89(3H, s),
4.12(1H, d, J=14 Hz), 4.36(1H, d, J=14 Hz),
5.03(1H, s), 5.07(2H, s),
5.09(2H, s), 5.67(1H, d, J=7 Hz),
6.72(2H, d, J=8.5 Hz), 7.29(2H, d, J=8.5 Hz)
8.13(1H, s), 8.28(1H, s),
9.05(1H, s),

EXAMPLE 24

7$\beta$-[D-2-(6,7-Bis(2,2,2-trichloroethoxy-carbonyloxy)-chromon-3-carboxamido)2-phenylacetamido]-7$\alpha$-methoxy-3-acetoxymethyl-3-cephem-4-carboxylic acid 7$\beta$-(D-2-amino-2-phenylacetamido)-7$\alpha$-methoxy-3-acetoxymethyl-3-cephem-4-carboxylic acid trifluoroacetic acid salt (22 mg) was suspended in 1 ml of tetrahydrofuran (1 ml). To the suspension, N,O-bis(trimethylsilyl)acetamide (43 $\mu$l) were added at 0° C. with stirring and further stirred at 0° C. for 2 minutes. To the mixture were further added 6,7-bis(2,2,2-trichloroethoxycarbonyloxy)chromon-3-carbonyl chloride (23.7 mg) dissolved in tetrahydrofuran (0.5 ml), and the whole was further stirred at 0° C. for 2 hours.

The reaction solution was concentrated to 0.5 ml, and poured to 0.5 N ice-cooled hydrochloric acid (10 ml). Precipitate separated out was recovered by filtration, washed with water and dried. The dry precipitate was washed with a 2% solution of tetrahydrofuran in ethyl ether, followed by ethyl ether and dried. There were thus obtained the desired product (7 mg).
Melting Point: 160°–240° C. (decomposition)
Infrared absorption, (cm$^{-1}$ Nujol): 1780, 1710–1740, 1660, 1610
NMR spectrums ($\delta$, DMSO-d$_6$):
2.00(3H, s), 3.41(3H, s),
4.62(1H, d, J=13 Hz), 4.90(1H, d, J=13 Hz),
5.09(5H, br, s), 5.84(1H, d, J=7.5 Hz), 7.2–75(5H, m), 8.15(1H, s)
8.30(1H, s), 9.06(1H, s)

Further compounds given in the following Examples 25–27 were also obtained in accordance with the methods similar to those mentioned in the above Examples 20–24.

EXAMPLE 25

7β-[D-2-(6,7-Bis(2,2,2-trichloroethoxycarbonyloxy)-chromone-3-carboxamido)-2-(4-hydroxyphenyl)acetamido]-7α-methoxy-3-acetoxymethyl-3-cephem-4-carboxylic acid Melting Point: 210°–230° C. (decomposition). Elemental analysis: for $C_{35}H_{27}Cl_6N_3O_{17}S$

|  | C | H | N |
|---|---|---|---|
| Calculated (%) | 41.77 | 2.70 | 4.18 |
| Found (%) | 41.72 | 2.70 | 4.36 |

Infrared absorption spectrum, (cm$^{-1}$, Nujol): 1780, 1765, 1660–1680, 1615
NMR spectrum, (δ, DMSO-d$_6$):
2.00(3H, s), 3.41(3H, s),
4.62(1H, d, J=13 Hz), 4.90(1H, d, J=13 Hz)
5.1(5H, br. s), 5.70(1H, d, J=7 Hz),
6.73(2H, d, J=8.5 Hz), 7.31(2H, d, J=8.5 Hz)
8.16(1H, s), 8.30(1H, s),
9.07(1H, s)

EXAMPLE 26

7β-[D-2-(6,7-Bis(2,2,2-trichloroethoxycarbonyloxy)-chromone-3-carboxamido)-2-(4-hydroxyphenyl)acetamido]-7α-methoxy-3-(1-methoxycarbonylmethyl-5-tetrazolyl)thiomethyl-3-cephem-4-carboxylic acid Melting Point: 155°–180° C. (decomposition) Elemental analysis: for $C_{37}H_{29}Cl_6N_7O_{17}S_2$

|  | C | H | N |
|---|---|---|---|
| Calculated (%) | 39.66 | 2.61 | 8.75 |
| Found (%) | 38.91 | 2.39 | 8.17 |

Infrared absorption spectrum, (cm$^{-1}$, Nujol): 1780, 1765, 1750, 1660
NMR spectrum, (δ, DMSO-d$_6$):
3.42(3H, s), 3.72(3H, s),
4.15(1H, d, J=14 Hz), 4.43(1H, d, J=14 Hz),
5.00(1H, s), 5.06(2H, s),
5.08(2H, s), 5.39(2H, br. s),
5.67(1H, d, J=7 Hz), 6.72(2H, d, J=8.5 Hz),
7.30(2H, d, J=8.5 Hz), 8.12(1H, s),
8.27(1H, s), 9.05(1H, s)

EXAMPLE 27

7β-[D-2-(6,7-Bis(ethoxycarbonyloxy)chromone-3-carboxamido)-2-(4-hydroxyphenyl)acetamido]-7α-methoxy-3-(1-carboxymethyl-5-tetrazolyl)thiomethyl-3-cephem-4-carboxylic acid Melting Point: 155°–230° C. (decomposition)
Infrared absorption spectrum (cm$^{-1}$, Nujol): 1740–1790, 1665, 1610
NMR spectrum (δ, DMSO-d$_6$):
1.32(6H, t, J=7 Hz), 3.42(3H, s),
4.05–4.55(6H, m), 5.00(1H, s),
5.28(2H, br. s), 5.67(1H, d, J=6.5 Hz),
6.71(2H, d, J=8 Hz), 7.29(2H, d, J=8 Hz),
7.99(1H, s), 8.15(1H, s),
9.03(1H, s)

EXAMPLE 28

7β-[D-2-(6,7-Dihydroxychromone-3-carboxamido)-2-(4-hydroxyphenyl)acetamido]-7α-methoxy-3-[5-carboxymethyl-2-(1,3,4-thiadiazolyl)]thiomethyl-3-cephem-4-carboxylic acid (a) 6,7-Dihydroxychromone-3-carbonyl chloride 6,7-Dihydroxychromone-3-carboxylic acid (888 mg) and 25 ml of thionyl chloride were refluxed for one hour. Then, the thionyl chloride was removed by distillation, and after benzene was added, further distillation was conducted. Dichloromethane was added into the residue for solidification, whereby the desired product (719 mg) was obtained.

Infrared Absorption Spectrum (cm$^{-1}$, nujol): 1780, 1765, 1645, 1625.

(b) 7β-[D-2-(6,7-Dihydroxychromone-3-carboxamido)-2-(4-hydroxyphenyl)acetamido]-7α-methoxy-3-acetoxymethyl-3-cephem-4-carboxylic acid 7β-[D-2-Amino-2-(4-hydroxyphenyl)acetamido]-7α-methoxy-3-acetoxymethyl-3-cephem-4-carboxylic acid trifluoroacetic acid salt (680 mg) was suspended in tetrahydrofuran (25 ml). Added into the suspension was N,O-bis(trimethylsilyl)acetamide (1.33 ml), and the mixture was stirred at 0° C. After 10 minutes, 6,7-dihydroxychromone-3-carbonylchloride (289 g) as mentioned in (a) above were added into the suspension, and it was stirred for two more hours at the same temperature. The reaction mixture was concentrated to about 10 ml, and the concentrate was poured into 0.5 N hydrochloric acid (100 ml) at 0° C. The resulting precipitate was collected by filtration, and washed with water. It was dissolved in tetrahydrofuran (100 ml), and the solution was dried over magnesium sulfate. After the solution was concentrated to about 10 ml, it was poured into ethyl ether (100 ml). The precipitate thereby formed was collected by filtration, and dried to yield the desired product (294 mg). The solvent was removed from the filtrate by distillation, and tetrahydrofuran and ethyl ether (0.2:9.8) were added to the residue for solidification, whereby the desired product (102 mg) was obtained, thereby making a total of the desired product (396 mg).

Melting Point: ca. 250° C. (decomposed). Elemental analysis: for $C_{33}H_{25}N_3O_{13}S$

|  | C | H | N |
|---|---|---|---|
| Calculated (%) | 56.33 | 3.58 | 5.97 |
| Found (%) | 51.78 | 3.90 | 6.22 |

Infrared Absorption Spectrum (cm$^{-1}$, nujol): 1770, 1720, 1710, 1615–1650.
NMR spectrum (δ, DMSO-d$_6$):
2.01(3H, s), 3.21(1H, br. d, J=18 Hz),
3.42(3H, s), 3.54(1H, br. d, J=18 Hz),
4.62(1H, d, J=13 Hz), 4.90(1H, d, J=13 Hz),
5.10(1H, s), 5.67(1H, d, J=7.5 Hz),
6.74(2H, d, J=9 Hz), 6.98(1H, s),
7.31(2H, d, J=9 Hz), 7.40(1H, s),
8.86(1H, s).

(c) 7β-[D-2-(6,7-Dihydroxychromone-3-carboxamido)-2-(4-hydroxyphenyl) acetamido]-7α-methoxy-3-

[5-carboxymethyl-2-(1,3,4-thiadiazolyl)]thiomethyl-3-cephem-4-carboxylic acid

The compound (131 mg) as mentioned in the preceding paragraph (b) and 2-mercapto-5-carboxymethyl-1,3,4-thiazole (70.4 mg) were dissolved in dimethylformamide (2.5 ml). To the solution was added dropwise phosphate buffer solution (pH 6.4) (5 ml) wherein of sodium hydrogencarbonate (110 mg) was dissolved. The resulting solution was then stirred at 70° C. for 5 hours. The reaction solution was cooled, then acidified with diluted hydrochloric acid. The precipitate crystallized out was recovered by filtration to obtain the desired product (49 mg).

Melting Point: 208°-220° C. (decomposed)
Infrared Absorption Spectrum (cm$^{-1}$, nujol): 1760, 1650, 1610
NMR Spectrum ($\delta$, DMSO-d$_6$):
3.42(3H, s), 4.18(2H, s),
5.03(1H, s), 5.66(1H, d, J=8 Hz),
6.71(2H, d, J=8 Hz), 6.96(1H, s),
7.30(2H, d, J=8 Hz), 7.39(1H, s),
8.82(1H, s)

EXAMPLE 29

7$\beta$-[D-2-(6,7-Dihydroxychromone-3-carboxamido)-2-(4-hydroxyphenyl)acetamido]-7$\alpha$-methoxy-3-[5-carboxymethyl-2-(1,3,4-oxadiazolyl)]thiomethyl-3-cephem-4-carboxylic acid The compound (131 mg) as mentioned in the paragraph (b) of the preceding Example 28 and 2-mercapto-5-carboxymethyl-1,3,4-oxadiazole (64 mg) were dissolved in dimethylformamide (2.5 ml). To the solution was added dropwise the phosphate buffer solution (pH 6.4) (5 ml) wherein sodium hydrogen carbonate (110 mg) was dissolved. The solution was stirred at 70° C. for 6 hours. The reaction solution was cooled, followed by pouring into diluted hydrochloric acid. The precipitate deposited out was recovered by filtration to obtain the desired product (64 mg).

Melting Point: 192°-195° C. (decomposed)
Infrared Absorption Spectrum (cm$^{-1}$, nujol): 1760, 1655, 1610
NMR Spectrum ($\delta$, DMSO-d$_6$):
3.41(3H, s), 4.01(2H, s),
5.07(1H, s), 5.67(1H, d, J=8 Hz),
6.72(2H, d, J=9 Hz), 6.98(1H, s),
7.25(2H, d, J=8 Hz), 7.40(1H, s),
8.85(1H, s)

EXAMPLE 30

7$\beta$-[D-2-(7,8-Dihydroxychromone-3-carboxamido)-2-phenylacetamido]-7$\alpha$-methoxy-3-[5-carboxymethyl-2-(1,3,4-thiadiazolyl)]thiomethyl-3-cephem-4-carboxylic acid (a) 7,8-Dihydroxychromone-3-carbonyl chloride 7,8-Dihydroxychromone-3-carboxylic acid (6.6 g) together with thionyl chloride (25 ml) were refluxed for one hour. Certain unreacted thionyl chloride remained in the reaction mixture was distilled off, and after addition of benzene to the residue, the mixture was again subjected to distillation. To the residue was added n-hexane to cause solidification of the residue. The solid matter thus formed was recovered by filtration. There was thus obtained the desired product (7.2 g).

Infrared Absorption Spectrum (cm$^{-1}$, nujol): 1775, 1660, 1620

(b) 7$\beta$-[D-2-(7,8-Dihydroxychromon-3-carboxyamido)-2-phenylacetamido]-7$\alpha$-methoxy-3-acetoxymethyl-3-cephem-4-carboxylic acid 7$\beta$-(D-2-Amino-2-phenylacetamido)-7$\alpha$-methoxy-3-acetoxymethyl-3-cephem-4-carboxylic acid trifluoro acetic acid salt (700 mg) was suspended in ethyl acetate (35 ml). To the suspension were added at 0° C. with stirring N,O-bis(trimethylsilyl)acetamide (2.20 ml). At 10 minutes' lapse, there was added 7,8-dihydroxychromone-3-carbonyl chloride (305.5 mg) obtained under the preceding paragraph (a). The mixture was agitated for one hour at 0° C. and then two hours at 15° C. Ethyl acetate (700 ml) were added to the reaction mixture, and the whole was successively washed with 140 ml each of 0.5 N hydrochloric acid, distilled water (twice) and a saturated aqueous solution of sodium chloride. Organic layer separated out was recovered and dried over magnesium sulfate. The solvent was then distilled off therefrom, and the residue was dissolved in acetone (70 ml) and the solution was allowed to stand at room temperature overnight. The solvent was distilled off from the solution, and the residue was solidified with addition of ethyl ether. The solid mass was washed with a mixture consisting of ethyl ether, acetone and methanol in the ratio of 9:0.5:0.5 by volume. There was thus obtained 175 mg of the desired product.

Melting Point: 200°-240° C. (decomposition) Elemental Analysis: for C$_{29}$H$_{25}$N$_3$O$_{12}$S,

|  | C | H | N |
|---|---|---|---|
| Calculated (%) | 54.46 | 3.94 | 6.57 |
| Found (%) | 53.75 | 4.01 | 6.23 |

Infrared Absorption Spectrum, (cm$^{-1}$, nujol): 1775, 1735, 1715, 1670, 1620
NMR Spectrum, ($\delta$, DMSO-d$_6$):
2.00(3H, s), 3.19(1H, d, J=18 Hz),
3.42(3H, s), 3.52(1H, d, J=18 Hz),
4.61(1H, d, J=13 Hz),
4.88(1H, d, J=18 Hz), 5.11(1H, s),
5.81(1H, d, J=7.5 Hz),
7.03(1H, d, J=8.5 Hz),
7.1-7.6(6H, m), 8.93(1H, s)

(c) 7$\beta$-[D-2-(7,8-Dihydroxychromone-3-carboxamido)-2-phenylacetamido]-7$\alpha$-methoxy-3-[5-carboxymethyl-2-(1,3,4-thiadiazolyl)]thiomethyl-3-cephem-4-carboxylic acid In the same manner as in Example 1, the compound (128 mg) of the preceding paragraph (b) and 2-mercapto-5-carboxymethyl-1,3,4-thiadiazole (70.4 mg) were reacted with each other, to obtain the desired product (44 mg).

Infrared Absorption Spectrum (cm$^{-1}$, nujol): 1760, 1650, 1610
NMR Spectrum ($\delta$, DMSO-d$_6$):
3.42(3H, s), 4.18(2H, s),
5.05(1H, s), 7.04(1H, d, J=8.5 Hz),
7.1-7.6(6H, m), 8.91(1H, s)

EXAMPLE 31

7$\beta$-[D-2-(6,7-Dihydroxychromone-3-carboxamido)-2-(4-hydroxyphenyl)acetamido]-7$\alpha$-methoxy-3-[1-[2-(N,N-dimethylamino)ethyl]-5-tetrazolyl]thiomethyl-3-cephem-4-carboxylic acid Compound (131.1 mg), which was obtained under Item (b) of Example 28, and 5-mercapto-1-[2-(N,N- dimethylamino)ethyl]tetrazole (52.0 mg) were dissolved in dimethylformamide (2.5 ml).

Another solution, which was obtained by dissolving sodium hydrogen carbonate (58.8 mg) in a phosphate buffer solution (5 ml), was introduced with stirring at 70° C. to the aforementioned solution, and the whole was stirred for seven hours at the temperature same as the above. The reaction liquor was cooled and poured into 0.2 N hydrochloric acid (50 ml). The precipitate separated out was collected by filtration, washed with water and dried.

There was thus obtained the desired product (35 mg).
Melting Point: 223°–225° C. (decomposition);
Infrared Absorption Spectrum (cm$^{-1}$, nujol): 1760, 1660, 1610, 1510;
NMR Spectrum ($\delta$, DMSO-d$_6$):
2.57(6H, s), 3.28(2H, t, J=6 Hz),
3.42(3H, s), 4.55(2H, t, J=6 Hz),
5.01(1H, s), 6.72(2H, t, J=8 Hz),
6.96(1H, s), 7.30(2H, d, J=8 Hz),
7.39(1H, s), 8.84(1H, s).

EXAMPLES 32–35

Further compounds given in the following Examples 32–35 were also obtained in accordance with the method similar to that of above Examples 28–31.

EXAMPLE 32

7$\beta$-[D-2-(6,7-Dihydroxychromone-3-carboxamido)-2-(4-hydroxyphenyl)acetamido]-7$\alpha$-methoxy-3-(1-ethyl-5-tetrazolyl)thiomethyl-3-cephem-4-carboxylic acid Melting Point: 205°–207° C. (decomposition);
Infrared Absorption Spectrum (cm$^{-1}$, nujol): 1760, 1660, 1610, 1515
NMR Spectrum, ($\delta$, DMSO-d$_6$):
1.38(3H, t, J=8 Hz), 3.42(3H, s),
4.27(2H, q, J=8 Hz), 5.02(1H, s),
5.66(1H, d, J=8 Hz), 6.75(2H, d, J=8 Hz),
6.96(1H, s), 7.32(2H, d, J=8 Hz),
7.39(1H, s), 8.82(1H, s)

EXAMPLE 33

7$\beta$-[D-2-(6,7-Dihydroxychromone-3-carboxamido)-2-(4-hydroxyphenyl)acetamido]-7$\alpha$-methoxy-3-[2-(1,3,4-thiadiazolyl)]thiomethyl-3-cephem-4-carboxylic acid Melting Point: 207°–209° C. (decomposition);
Infrared Absorption Spectrum, (cm$^{-1}$, nujol): 1760, 1650, 1605, 1505;
NMR Spectrum, ($\delta$, DMSO-d$_6$),:
3.41(3H, s), 4.16(1H, d, J=13 Hz),
4.56(1H, d, J=13 Hz), 5.05(1H, s),
5.66(1H, d, J=7 Hz), 6.72(2H, d, J=8 Hz),
6.96(1H, s), 7.29(2H, d, J=8 Hz),
7.39(1H, s), 8.84(1H, s),
9.51(1H, s).

EXAMPLE 34

7$\beta$-[D-2-(6,7-Dihydroxychromone-3-carboxamido)-2-(4-hydroxyphenyl)acetamido]-7$\alpha$-methoxy-3-[5-methyl-2-(1,3,4-oxadiazolyl)]thiomethyl-3-cephem-4-carboxylic acid Melting Point: 215°–218° C. (decomposition);
Infrared Absorption Spectrum, (cm$^{-1}$, nujol): 1770, 1660, 1610, 1520;
NMR Spectrum, ($\delta$, DMSO-d$_6$);
2.45(3H, s), 3.41(3H, s),
4.07(1H, d, J=13 Hz), 4.36(1H, d, J=13 Hz),
5.04(1H, s), 5.66(1H, d, J=7 Hz),
6.73(2H, d, J=8 Hz), 6.96(1H, s),
7.27(2H, d, J=8 Hz), 7.39(1H, s),
8.84(1H, s).

EXAMPLE 35

7$\beta$-[D-2-(6,7-Dihydroxychromone-3-carboxamido)-2-(4-hydroxyphenyl)acetamido]-7$\alpha$-methoxy-3-carboxymethylthiomethyl-3-cephem-4-carboxylic acid Infrared Absorption Spectrum, (cm$^{-1}$, nujol),: 1740–1780, 1660, 1610;
NMR Spectrum, ($\delta$, DMSO-d$_6$),:
3.2–3.85(6H, m), 3.41(3H, s),
5.07(1H, s), 5.67(1H, d, J=7 Hz),
6.75(2H, d, J=8.5 Hz), 6.99(1H, s),
7.30(2H, d, J=8.5 Hz), 7.40(1H, s),
8.85(1H, s).

EXAMPLE 36

7$\beta$-[D-2-(6,7-Dihydroxychromone-3-carboxyamido)-2-(4-hydroxyphenyl)acetamido]-7$\alpha$-methoxy-(1-ethyl-5-tetrazolyl)thiomethyl-3-cephem-4-carboxylic acid 7$\beta$-[D-2-Amino-2-(4-hydroxyphenyl)acetamido]-7$\alpha$-methoxy-3-(1-ethyl-5-tetrazolyl)thiomethyl-3-cephem-4-carboxylic acid trifluoroacetic acid salt (127 mg) was suspended into ethyl acetate (7 ml). To the resulting suspension was added drop by drop with stirring at 0° C. N,O-bis(trimethylsilyl)acetamide (346 $\mu$l), and stirring was continued at 0° C. for 20 minutes. There was added the carboxylic acid chloride (48 mg), which was obtained under Item (a) of Example 28, and the whole was further stirred for two hours at 0° C.

To the reaction liquor thus obtained was added ethyl acetate (150 ml), and the organic layer recovered therefrom was successively washed with 30 ml each of 0.5 N hydrochloric acid and distilled water (three times), dried over magnesium sulfate, and the solvent was removed therefrom by distillation. The residual matter was dissolved in aceton (30 ml) and the solution was allowed to stand overnight. The solvent was distilled off therefrom, and the residue was solidified with addition of ethyl ether. The solid substance collected was washed with a mixture consisting of ethyl ether, acetone and methanol (9:1:1). When dried, there was obtained the desired product (41 mg).

The product showed the melting point, infrared absorption spectrum and NMR spectrum same as those shown by the product obtained in Example 32.

EXAMPLE B 37

7$\beta$-[D-2-(6,7-Dihydroxychromone-3-carboxamido)-2-(4-hydroxyphenyl)acetamido]-7$\alpha$-methoxy-3-(1-carboxymethyl-5-tetrazolyl)thiomethyl-3-cephem-4-carboxylic acid 7$\beta$-[D-2-Amino-2-[4-hydroxyphenyl)acetamido]-7$\alpha$-methoxy-3-(1-carboxymethyl-5-tetrazolyl)thiomethyl-3-cephem-4-carboxylic acid trifluoroacetic acid salt (301.2 mg) was suspended into tetrahydrofuran (15 ml). To the suspension was added N,O-bis(trimethylsilyl)acetamide (503 $\mu$l) at 0° C. with stirring. The mixture was stirred for 20 minutes at room temperature, followed by cooling it to 0° C. To the mixture was then added the acid chloride (109.1 mg) obtained in (a) of Example 3, and the whole was stirred at 0° C. for 2 hours. The reaction solution was concentrated to about 7 ml, and the concentrate was poured into 1 N hydrochloric acid (50 ml)-ice-cooled water (100 ml). The resulting precipitate was recovered by filtration, followed by washing with water. The product was dissolved in tetrahydrofuran (100 ml), and the solution was dried over magnesium sulfate. The solution was concentrated to about 5 ml. The concentrate was poured into ethylether (100 ml). The resulting precipitate was recovered by filtration, followed by drying to obtain the desired compound (203.6 mg). Also, the desired compound (40.6 mg) was recovered from the above filtrate.

Melting point, infrared absorption spectrum and NMR spectrum of the compound were agreed with those of the compound which was obtained in Example 15.

EXAMPLE 38

7β-[D-2-(6,7-Dihydroxychromone-3-carboxamido)-2-(4-hydroxyphenyl)acetamido]-7α-methoxy-3-(1-carboxymethyl-5-tetrazolyl)thiomethyl-3-cephem-4-carboxylic acid The compound (35 mg) obtained in Example 19 was dissolved in methanol (1 ml). To the solution was added dropwise aqueous solution (1.37 ml) of 1 N sodium hydroxide. After 20 minutes, 0.1 N sodium hydroxide (40 μl) was further added to the above solution. The pH value of the reaction solution was adjusted to about 7 with the addition of 1 N hydrochloric acid. The most portion of methanol was distilled off at room temperature under reduced pressure. The pH value of the solution was then adjusted to about 2.5 with the addition of 1 N hydrochloric acid. The resulting precipitate was collected by filtration, and washed with water and then ethylether, followed by drying to obtain the desired product (25 mg).

Melting point, infrared absorption spectrum and NMR spectrum of the product were agreed with those of the compound which was obtained in Example 15.

The compounds obtained in these examples were tested for their antibacterial activities in vitro.

METHOD

Minimal inhibitory concentration (MIC) was determined by the standard agar dilution method of the Japan Society of Chemotherapy.

Compounds were dissolved in appropriate solvents (sterilized water for sodium salts and acetone-water [1:1] for free acids) and serial two-fold dilutions were made. Sodium salt of Cefazolin was chosen as the control compound.

One-ml aliquots of each dilution were mixed with 9 ml of Mueller Hinton gar in petri-dishes to make agar plates containing the compound at serially diluted concentrations. After agar hardened, plates were put in an incubator at 37° C. for 1.5–2 hours with the lids slightly open to evaporate acetone off the plates.

Test organisms were grown for 18 hours at 37° C. in Trypticase Soy broth and diluted in saline to approximately $10^6$ colony forming units per ml. A loopful of each cell suspension was applied on the agar plate mentioned above and the plates were incubated for 18 hours at 37° C. before MIC was determined.

The results are shown in Table 2, wherein the compound of Example 5 was selected and used in a form of free carboxylic acid as set forth in the Example 5, Item (a).

TABLE II

| Test compound | | Staphylococcus aureus 209-P | Escherichia coli NIHJ | Klebsielle pneumoniae EK-6 | Proteus morganii EP-14 | Pseudomonas aeruginosa EP-172 | Serratia marcescens ES-75 | Proteus bulgaris E-18 |
|---|---|---|---|---|---|---|---|---|
| | | | | MIC (μg/ml) Test bacteria | | | | |
| Example | 1 | 1.56 | 0.4 | ≦0.1 | 3.13 | 0.4 | ≦0.1 | 0.4 |
| | 2 | 1.56 | 3.13 | ≦0.1 | 50 | 0.8 | 0.8 | 6.25 |
| | 3 | 3.13 | 0.4 | ≦0.1 | 3.13 | 0.8 | ≦0.1 | 0.8 |
| | 4 | 3.13 | 3.13 | ≦0.1 | 50 | 0.8 | 0.8 | 3.13 |
| | 5 | 3.13 | 0.8 | ≦0.1 | 25 | 3.13 | 0.2 | 0.8 |
| | 6 | 3.13 | 0.8 | ≦0.1 | 12.5 | 3.13 | ≦0.1 | 0.8 |
| | 7 | 6.25 | 3.13 | 0.2 | 100 | 3.13 | 12.5 | 50 |
| | 10 | 0.4 | 12.5 | 12.5 | 25 | 25 | 12.5 | 50 |
| | 13 | 0.4 | 3.13 | 3.13 | 1.56 | 12.5 | 3.13 | 0.8 |
| | 15 | 6.25 | 6.25 | ≦0.1 | 12.5 | 3.13 | 0.4 | 1.56 |
| | 18 | 25 | 25 | 0.8 | 50 | 6.25 | 3.13 | 6.25 |
| | 19 | 3.13 | 1.56 | ≦0.1 | 1.56 | 0.8 | ≦0.1 | 0.4 |
| | 20 | 6.25 | 3.13 | ≦0.1 | 6.25 | 0.4 | 0.2 | 0.8 |
| | 22 | 1.56 | 6.25 | ≦0.1 | 25 | 0.8 | 0.4 | 1.56 |
| | 23 | 3.13 | 6.25 | ≦0.1 | 6.25 | 0.8 | 0.2 | 0.8 |
| | 24 | 6.25 | 12.5 | ≦0.1 | 25 | 1.56 | 0.8 | 3.13 |
| | 25 | 3.13 | 12.5 | ≦0.1 | 25 | 0.8 | 0.8 | 3.13 |
| | 26 | 12.5 | 6.25 | ≦0.1 | 6.25 | 1.56 | 0.2 | 0.8 |
| | 27 | 3.13 | 3.13 | ≦0.1 | 6.25 | 0.8 | 0.2 | 0.8 |
| | 28 | 3.13 | 3.13 | ≦0.1 | 12.5 | 0.8 | 0.4 | 1.56 |
| | 29 | 6.25 | 12.5 | ≦0.1 | 25 | 0.8 | 0.8 | 3.13 |
| | 31 | 3.13 | 12.5 | ≦0.1 | 25 | 0.8 | 0.4 | 3.13 |
| | 32 | 1.56 | 3.13 | ≦0.1 | 12.5 | 0.4 | 0.2 | 1.56 |
| | 33 | 1.56 | 6.25 | ≦0.1 | 25 | 0.4 | 0.2 | 1.56 |
| Control** | | 0.4 | 1.56 | 1.56 | >100 | >100 | >100 | >3200 |

*β-Lactamase-yielding bacterium
**Sodium salt of cephasoline

EXAMPLE 39

| Formulation of the tablet | |
|---|---|
| The compound of Example 2 | 250 mg |
| Cristallized cellulose | 80 mg |
| Calcium salt of carboxymethyl- | 38 mg |

-continued

| Formulation of the tablet | |
|---|---|
| cellulose | |
| Calcium stearate | 2 mg |
| One tablet | 370 mg |

The tablets were prepared using the above formulation by conventional processes.

EXAMPLE 40

| Formulation of the tablet | |
|---|---|
| The compound of Example 15 | 250 mg |
| Crystallized cellulose | 80 mg |
| Calcium salt of carboxymethyl-cellulose | 38 mg |
| Calcium stearate | 2 mg |
| One tablet | 370 mg |

The tablets were prepared using the above formulation by conventional processes.

EXAMPLE 41

| Formulation of the tablet | |
|---|---|
| The compound of Example 28 | 250 mg |
| Crystallized cellulose | 80 mg |
| Calcium salt of carboxymethyl-cellulose | 38 mg |
| Calcium stearate | 2 mg |
| One tablet | 370 mg |

The tablets were prepared using the above formulation by conventional processes.

What is claimed is:

1. A 7α-methoxycephalosporin derivative represented by the formula

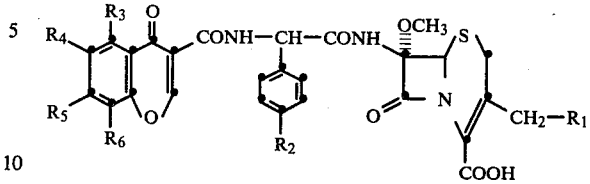

wherein $R_1$ represents lower alkanoyloxy; $R_2$ represents hydrogen or hydroxy; and $R_3$, $R_4$, $R_5$ and $R_6$ each represents a group selected from the class consisting of hydrogen, hydroxy, lower alkanoyloxy, methoxy, ethoxy, propoxy, methyl, ethyl, n-propyl, i-propyl, n-butyl, t-butyl, halogen, benzyloxy, phenethyloxy, nitro, methoxycarbonyloxy, ethoxycarbonyloxy and 2,2,2-trichloroethoxycarbonyloxy or a pharmaceutically acceptable salt thereof.

2. A compound according to claim 1 wherein $R_1$ is acetoxy.

3. A compound according to claim 2 wherein said compound is 7β-[D-2-(6,7-dihydroxychromone-3-carboxamido)-2-(4-hydroxyphenyl)acetamido]-7α-methoxy-3-acetoxymethyl-3-cephem-4-carboxylic acid or a sodium salt thereof.

4. A compound according to claim 2, wherein said compound is 7β-[D-2-(6,7-dihydroxychromone-3-carboxamido)-2-phenylacetamido]-7α-methyl-3-acetoxymethyl-3-cephem-4-carboxylic acid or a sodium salt thereof.

5. An antibacterial preparation which comprises an antibacterially effective amount of a compound according to claim 1 or a pharmaceutically acceptable salt thereof, together with a pharmaceutically acceptable carrier therefor.

* * * * *